US010856822B2

(12) United States Patent
Youd et al.

(10) Patent No.: US 10,856,822 B2
(45) Date of Patent: Dec. 8, 2020

(54) CLAMPING DEVICE FOR A PORTABLE X-RAY IMAGING DEVICE

(71) Applicant: Turner Imaging Systems, Inc., Orem, UT (US)

(72) Inventors: Thomas L. Youd, Salt Lake City, UT (US); Douglas P. Hansen, Spanish Fork, UT (US); Casey Owen Messick, Pleasant Grove, UT (US)

(73) Assignee: Turner Imaging Systems, Inc., Orem, UT (US)

( * ) Notice: Subject to any disclaimer, the term of this patent is extended or adjusted under 35 U.S.C. 154(b) by 0 days.

(21) Appl. No.: 16/453,533

(22) Filed: Jun. 26, 2019

(65) Prior Publication Data
US 2020/0196966 A1    Jun. 25, 2020

Related U.S. Application Data

(63) Continuation-in-part of application No. 16/199,070, filed on Nov. 23, 2018, now Pat. No. 10,674,974.

(51) Int. Cl.
*A61B 6/00* (2006.01)

(52) U.S. Cl.
CPC .......... *A61B 6/4441* (2013.01); *A61B 6/4225* (2013.01); *A61B 6/4405* (2013.01); *A61B 6/4452* (2013.01)

(58) Field of Classification Search
CPC .... A61B 6/4405; A61B 6/4411; A61B 6/4441
See application file for complete search history.

(56) References Cited

U.S. PATENT DOCUMENTS

| 2,355,066 | A | 8/1944 | Goldfield et al. |
| 5,499,284 | A | 3/1996 | Pellegrino et al. |
| 2008/0020332 | A1 | 1/2008 | LaVenda et al. |
| 2012/0076264 | A1 | 3/2012 | Ohta et al. |

(Continued)

FOREIGN PATENT DOCUMENTS

WO        0019781 A2    4/2000

OTHER PUBLICATIONS

The International Search Report and the Written Opinion of the International Searching Authority, PCT Application Serial No. PCT/US19/62650 (dated Feb. 5, 2020) 14 pages.

*Primary Examiner* — Mark R Gaworecki
(74) *Attorney, Agent, or Firm* — Kenneth E. Horton; Kirton McConkie

(57) ABSTRACT

Clamping devices used to assist with operating small, portable x-ray devices are described in this application. In particular, this application describes clamping devices used to connect portable X-ray devices to external support structures. The clamping devices contain a cradle configured to support a portion of a C-arm of a portable x-ray device, the cradle comprising a restraint configured to fit in an upper opening of the C-arm, a mounting plate configured to support a bottom portion of the portable x-ray device, a registration insert configured to mate with an opening in the bottom portion of the portable x-ray device, the registration insert also configured to move laterally along the mounting plate, a connecting member configured to move laterally along the mounting plate, and an attachment device configured to move the connecting member and the registration insert to attach the portable x-ray device to the cradle. Other embodiments are described.

20 Claims, 23 Drawing Sheets

(56) References Cited

U.S. PATENT DOCUMENTS

| | | |
|---|---|---|
| 2012/0148031 A1 | 6/2012 | Eaves et al. |
| 2014/0177797 A1 | 6/2014 | Ogura et al. |
| 2018/0108447 A1 | 4/2018 | Turner |
| 2019/0175128 A1 | 6/2019 | Eaves et al. |

CLAMPING DEVICE FOR A PORTABLE X-RAY IMAGING DEVICE

CROSS-REFERENCE TO RELATED APPLICATION

This patent application is a continuation-in-part of U.S. application Ser. No. 16/199,070, filed on Nov. 23, 2018, the entire disclosure of which is hereby incorporated by reference.

FIELD

This application relates generally to X-ray equipment. More specifically, this application relates to clamping devices that are used to assist with the operation of small, portable x-ray devices.

BACKGROUND

X-ray imaging systems typically contain an X-ray source and an X-ray detector. X-rays (or other types of radiation) are emitted from the source and impinge on the X-ray detector to provide an X-ray image of the object or objects that are placed between the X-ray source and the detector. The X-ray detector is often an image intensifier or even a flat panel digital detector. In some configurations, these devices contain a C-arm assembly with the source and detector on opposite ends of the "C" arm of the assembly. The C-arm assembly can move through continuous rotation angles relative to the object in order to acquire images from multiple orientations.

Some X-ray imaging systems have limited mobility since they contain a gantry that is secured to a floor, wall, or ceiling. Other imaging systems are more portable since they contain a mobile base (on wheels) and so they can be used in a variety of clinical environments, such as radiology and surgery departments of a medical facility. In either case, the gantry or mobile base is attached to the X-ray imaging device in a permanent or semi-permanent fashion, such that removing the C-arm from the supporting assembly is not done routinely and quickly.

SUMMARY

This application relates generally to clamping devices that are used to assist with the operation of small, portable x-ray devices. In particular, this application describes clamping devices used to connect a portable X-ray device to an external support structure. The clamping devices contain a cradle configured to support a portion of a C-arm of a portable x-ray device, the cradle comprising a restraint configured to fit in an upper opening of the C-arm, a mounting plate configured to support a bottom portion of the portable x-ray device, a registration insert configured to mate with an opening in the bottom portion of the portable x-ray device, the registration insert also configured to move laterally along the mounting plate, a connecting member configured to move laterally along the mounting plate, and an attachment device configured to move the connecting member and the registration insert to attach the portable x-ray device to the cradle. Using such a clamping device allows the portable x-ray device to be quickly and easily attached to, and detached from, the external support structure by the average person using only a single hand, while also preventing the portable x-ray device from accidentally being removed from the support structure.

BRIEF DESCRIPTION OF THE DRAWINGS

The following description can be better understood in light of the Figures which show various embodiments and configurations of the X-ray devices.

Figure 1:
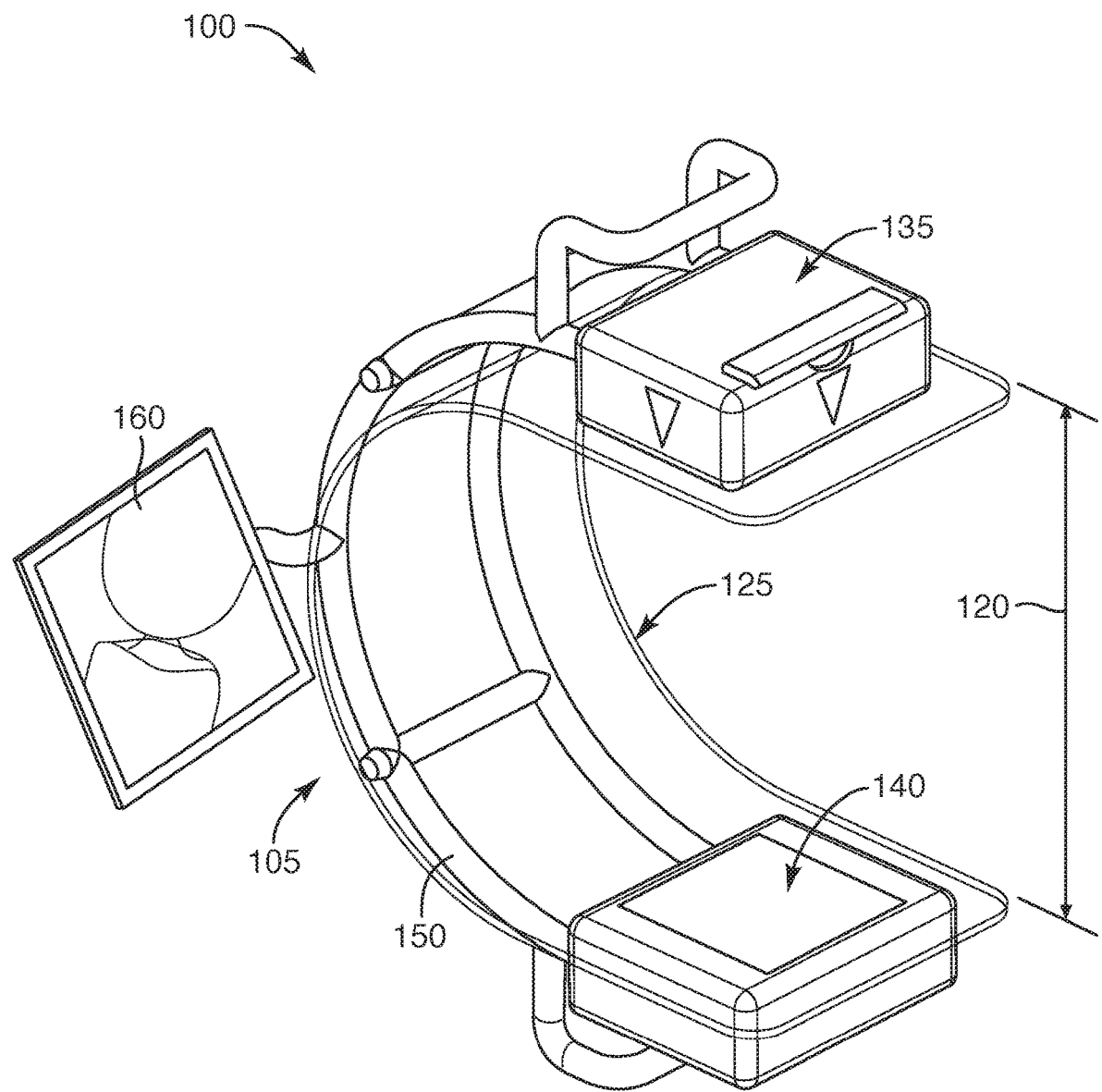
FIG. 1 shows a view of some embodiments of small, portable X-ray devices.

Together with the following description, the Figures demonstrate and explain the principles of the structures, methods, and systems described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described X-ray devices can be implemented and used without employing these specific details. Indeed, the described systems and methods related to X-ray devices can be placed into practice by modifying the described systems and methods and can be used in conjunction with any other apparatus and techniques conventionally used in the industry. For example, while the description below focuses on clamping mechanisms for C-arm x-ray devices, the clamping mechanisms can be used with other X-ray imaging arms and x-ray devices, including U-arms or portable x-ray devices that are configured to approximate the C-arm configuration.

In addition, as the terms on, disposed on, attached to, connected to, or coupled to, etc. are used herein, one object (e.g., a material, element, structure, member, etc.) can be on, disposed on, attached to, connected to, or coupled to another object—regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

FIG. 1 shows some embodiments of small, portable X-ray devices 100 that can be attached to and held by the supporting devices described herein. Generally, the portable X-ray devices 100 contain an imaging arm that allows the system to be used to take X-ray images of a portion of a patient's body or any other object capable of being analyzed by x-rays, including animals, industrial components such as electronic circuit boards, containers to be inspected, and/or passenger luggage. In some configurations, the imaging arm is substantially shaped like the letter "C" and is therefore referred to as a C-shaped support arm (or C-arm) 105. The C-arm has any size that can be held and operated by hand when in use, as seen in FIG. 1.

The C-arm 105 can contain any X-ray source 135 and X-ray detector 140 that allow the X-ray system 100 to take X-ray images. The X-ray source 135 can contain any source that generates and emits X-rays, including a standard stationary anode X-ray source, a microfocus x-ray source, a rotating anode x-ray source, and/or a fluoroscopic X-ray source. And the X-ray detector 140 can contain any detector that detects X-rays, including an image intensifier, a CMOS camera and/or a digital flat panel detector. In some configurations, the detector can have a substantially square shape with a length of one side ranging from about 13 cm to about 15 cm. In other configurations, the detector can have a substantially rectangular shape with the shorter dimension ranging from 12 cm to 16 cm, and the longer dimension ranging from 18 cm to 24 cm. The X-ray source 135 can be contained in a housing that can be configured in two parts with a first part enclosing the x-ray source 135 and a second, separate part enclosing the x-ray detector 140. In other configurations, however, the housing can be configured so that it is a single part that encloses both the X-ray source 135 and the X-ray detector 140.

In some configurations, the housing can also enclose a removable power source (such as a battery) and optionally a power supply. Thus, the power source and the power supply can be located internal to the housing and also to the x-ray device 100. The supporting electronics for the power source and the power supply, as well as the supporting electronics for an image display and for wireless data upload, can also be located internal to the housing. Thus, in these configurations, the x-ray device 100 does not contain an external power cord or data cable. Incorporating the power source (i.e., the battery), the power supply, and the supporting electronics all within the housing allows the size and the weight of the device to be reduced. With such a configuration, the power source can easily be replaced and delivers 60 or more x-ray images using a single charge. Of course, if needed, the x-ray device can be configured so that it is alternately, or additionally, charged using external power from a power cord that is plugged into a wall outlet. In other configurations, multiple power supplies can be provided for the source, detector, and control electronics, any (or all) of which can be located either internal or external to the housing.

The X-ray device 100 also contains a frame 150 that has an open configuration. As shown in FIG. 1, an open configuration gives a number of easy gripping options for a user to carry and hold the frame 150 during transport, and optionally during operation of the x-ray device 100. In some embodiments, the frame 150 can be configured as a modular unit so different cross members (or length member or handles) can be used to replace the existing cross members (or length member or handles). Thus, the frame 150 provides the ability for a user (or operator) to grip and hold the X-ray device 100 during operation, a feature that is useful since other conventional C-arms can't be held in the hands while being operated because they do not have a suitable frame and because they are too heavy.

Figure 2:
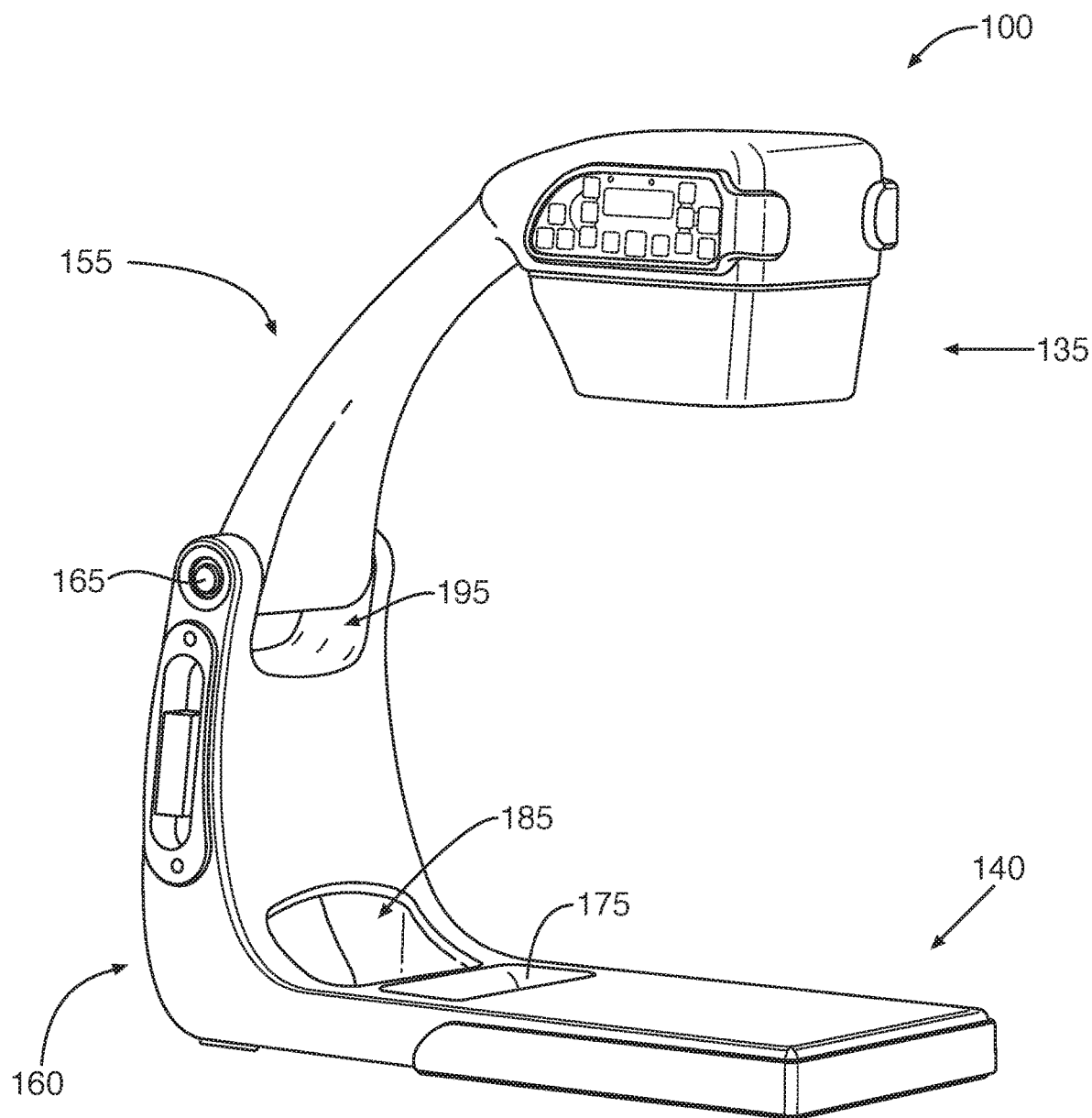
FIG. 2 shows another view of some embodiments of small, portable X-ray devices.

In other embodiments, the portable x-ray device has the configuration as illustrated in FIG. 2. In the embodiments of FIG. 2, the frame 150 has a first portion 155 that is part of the housing that also contains the x-ray source 135 and the associated electronics. The frame 150 also has a second portion 160 that is part of the housing that also contains the x-ray detector 140 and the associated electronics. The first portion 155 of the housing and the second portion 160 of the housing are connected using hinge 165. The bottom of the portable x-ray device can contain an opening 175.

The portable x-ray device 100 has several features not exhibited by other C-arm devices. First, it has the capability of wireless data transfer, thereby eliminating the need for any wired connections or cables to the C-arm. Second, it is internally powered by a battery or internal power source and, therefore, more portable than other C-arm devices which require a power cable. Third, it is lighter than other C-arm devices. As a comparison, the portable x-ray C-arm devices 100 described herein can have a weight ranging from about 10 to about 25 pounds while other C-arm devices have a weight ranging from about 35 to about 375 pounds. In other embodiments, the portable x-ray C-arm devices 100 described herein can have a weight ranging from about 12 to about 18 pounds.

Figure 3A:
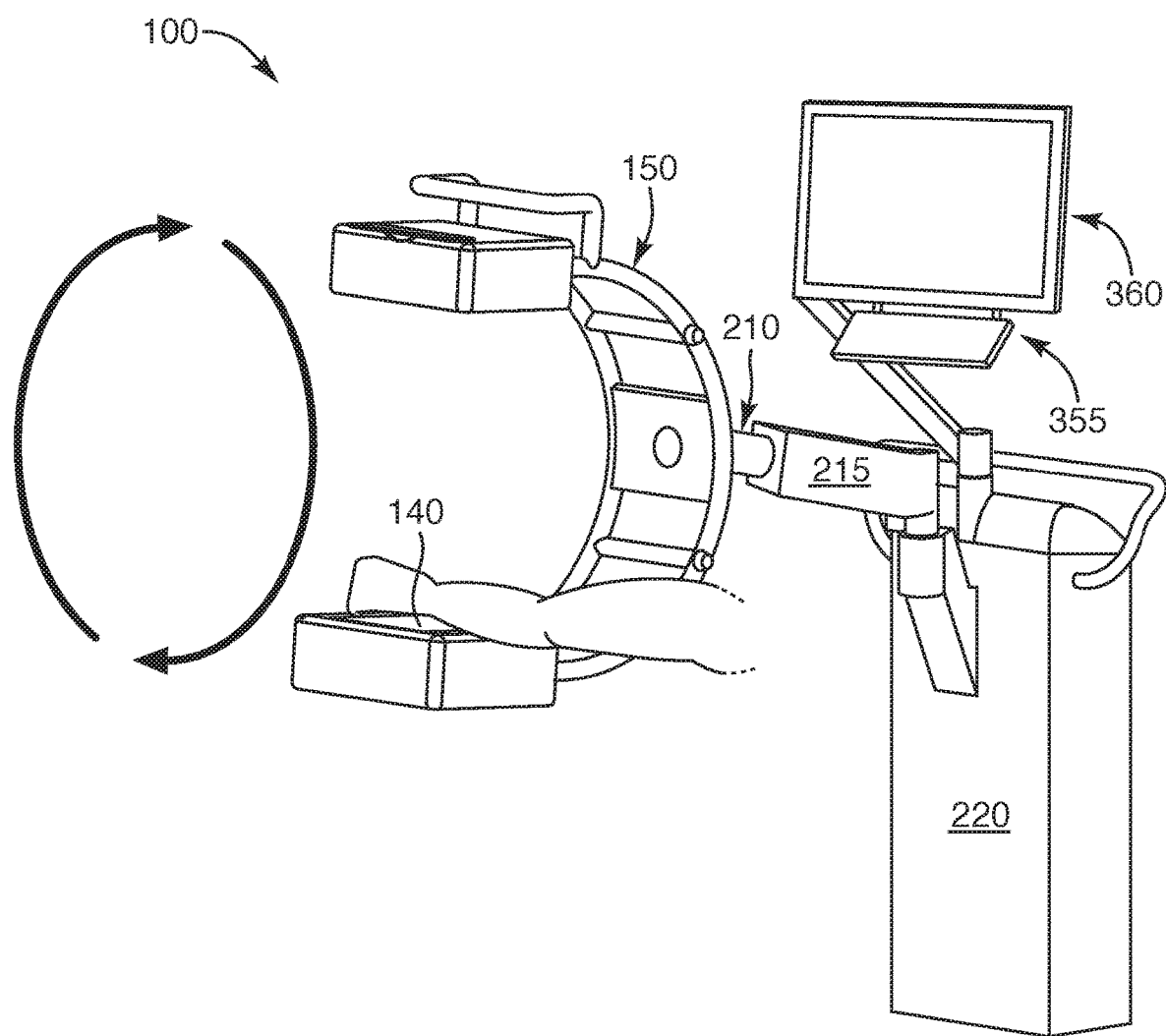
FIGS. 3A and 3B show some embodiments of supporting devices that can be used with small, portable X-ray devices.
Figure 3B:
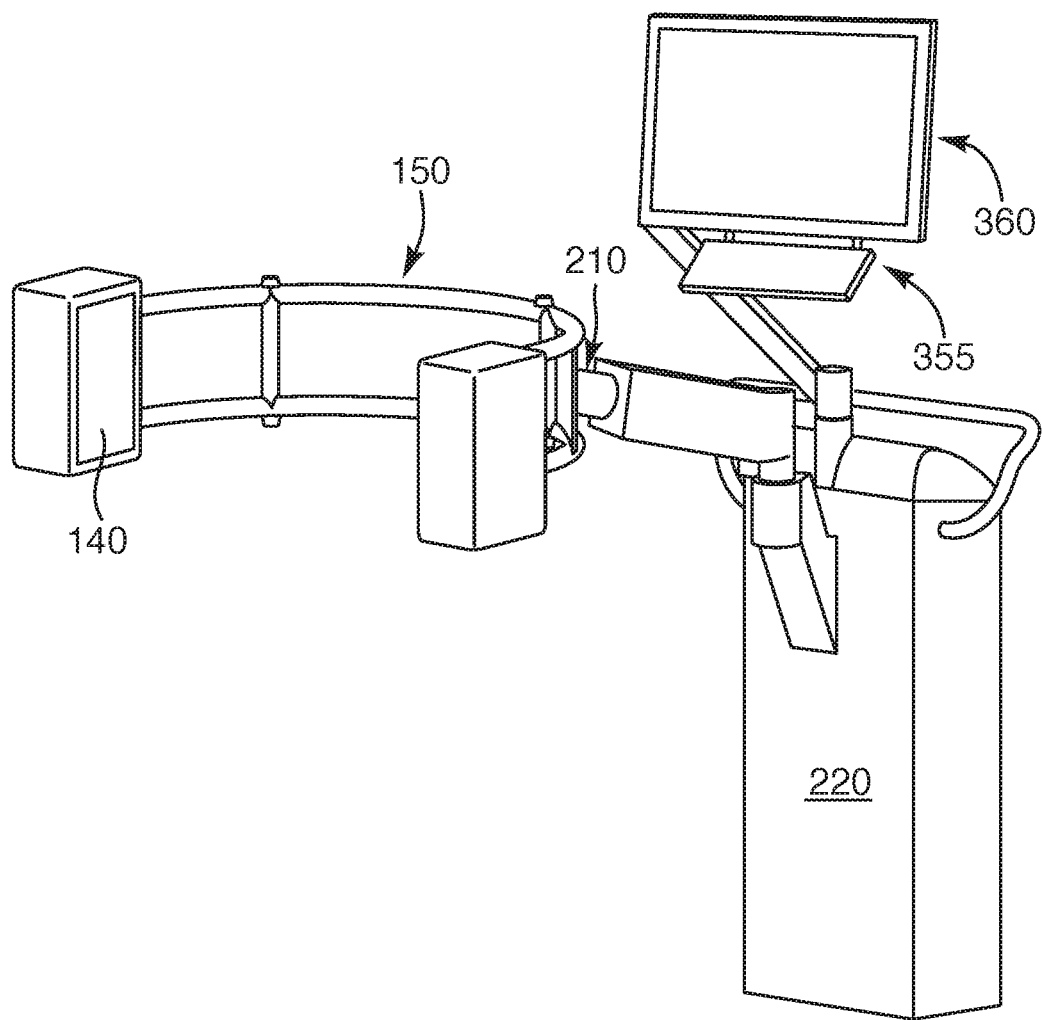
Figure 4:
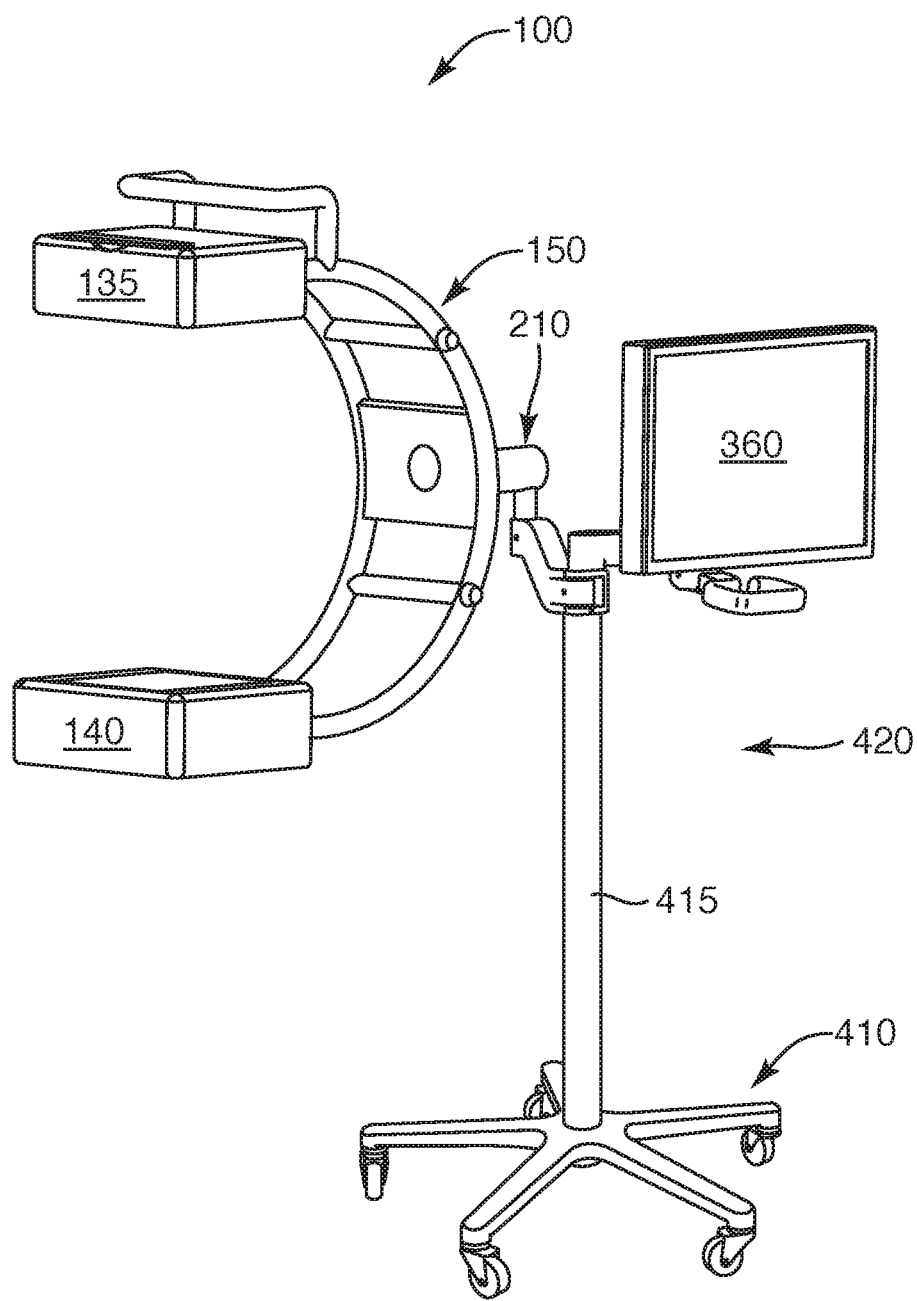
FIG. 4 shows other embodiments of supporting devices that can be used with small, portable X-ray devices.
Figure 5:
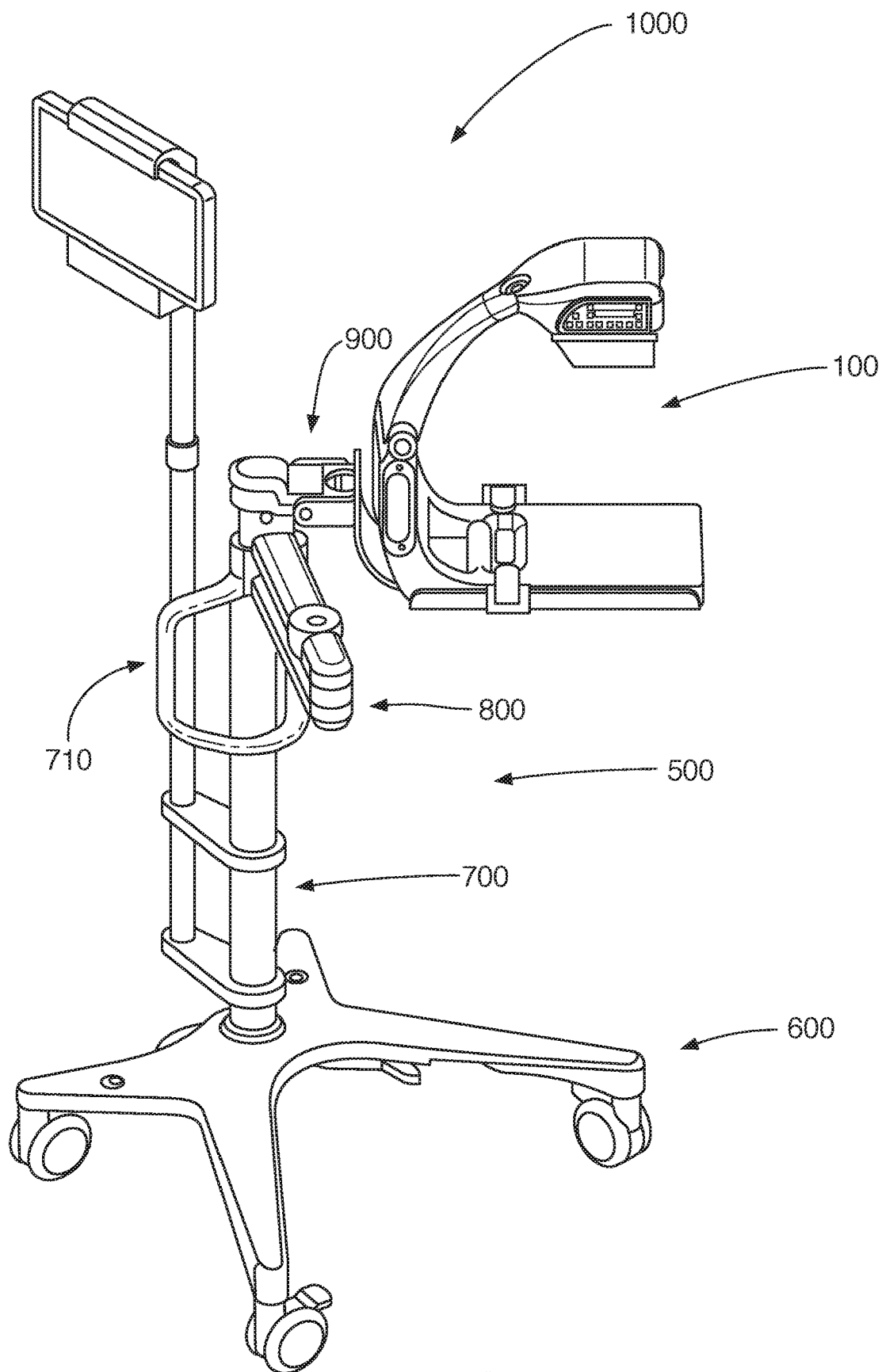
FIG. 5 illustrates yet other embodiments of a supporting device for holding small, portable X-ray devices.

In some embodiments, the portable x-ray device 100 can be connected to a stationary external (or support) structure so that it can rotate, or be positioned, around an object being analyzed, as shown in FIGS. 3A and 3B and as described in U.S. patent application Ser. No. 15/568,708, filed Nov. 23, 2017, the entire disclosure of which is incorporated herein by reference. In other embodiments, the portable x-ray device 100 can be connected to a mobile external (or support) structure for a similar purpose, as shown in FIGS. 4 and 5 and as described in U.S. patent application Ser. No. 16/198,956, filed Nov. 23, 2018, the entire disclosure of which is incorporated herein by reference. Attaching the portable x-ray device to a support structure allows the operator to position the portable x-ray device 100 as needed for a series of imaging procedures, while freeing medical personnel to attend to other duties. As well, it leaves the hands of the operator free for other actions. For example, during a surgical procedure, attaching the portable x-ray device 100 to a support structure allows the medical person to take many actions, but then easily image the patient when needed using the pre-selected positioning of the portable x-ray device 100. When the surgical procedure is complete, the portable x-ray device 100 can be removed from the support structure and taken to another location for use or storage.

Figure 13:
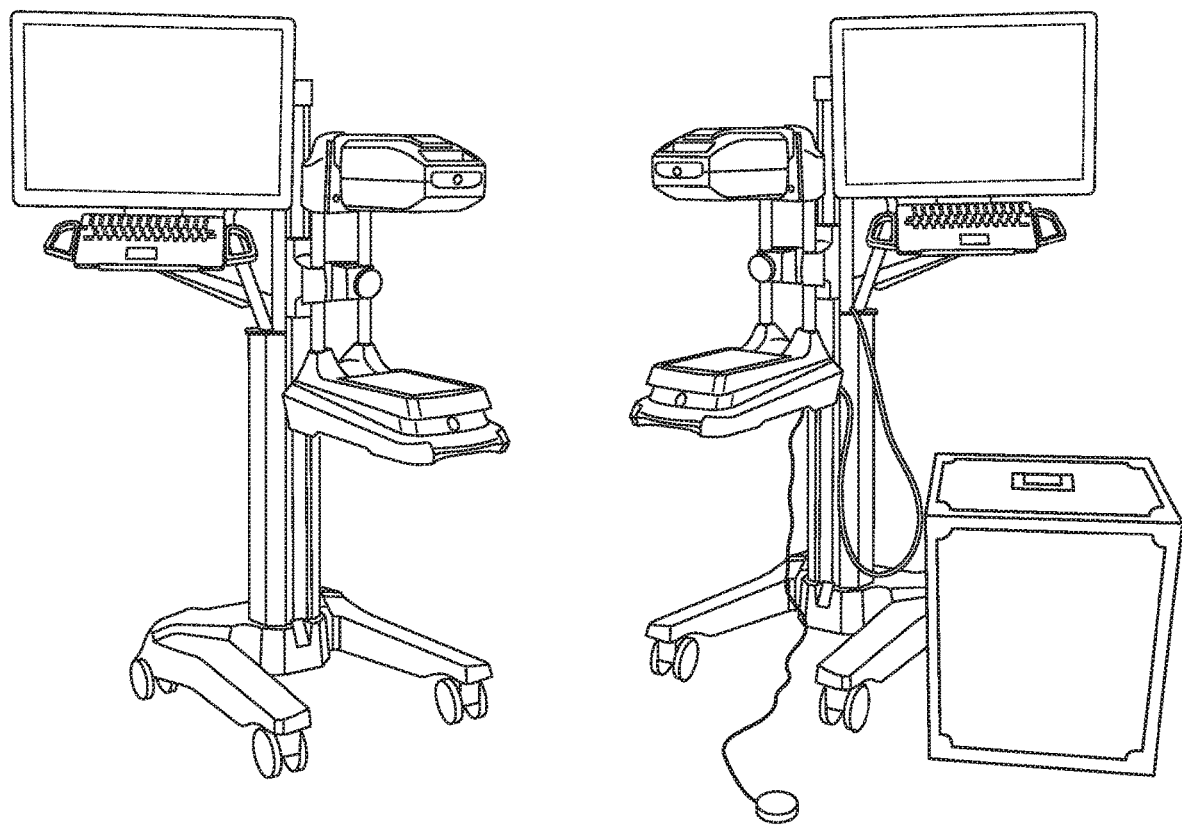
FIGS. 13-14 show some conventional supporting devices for x-ray devices.
Figure 14:
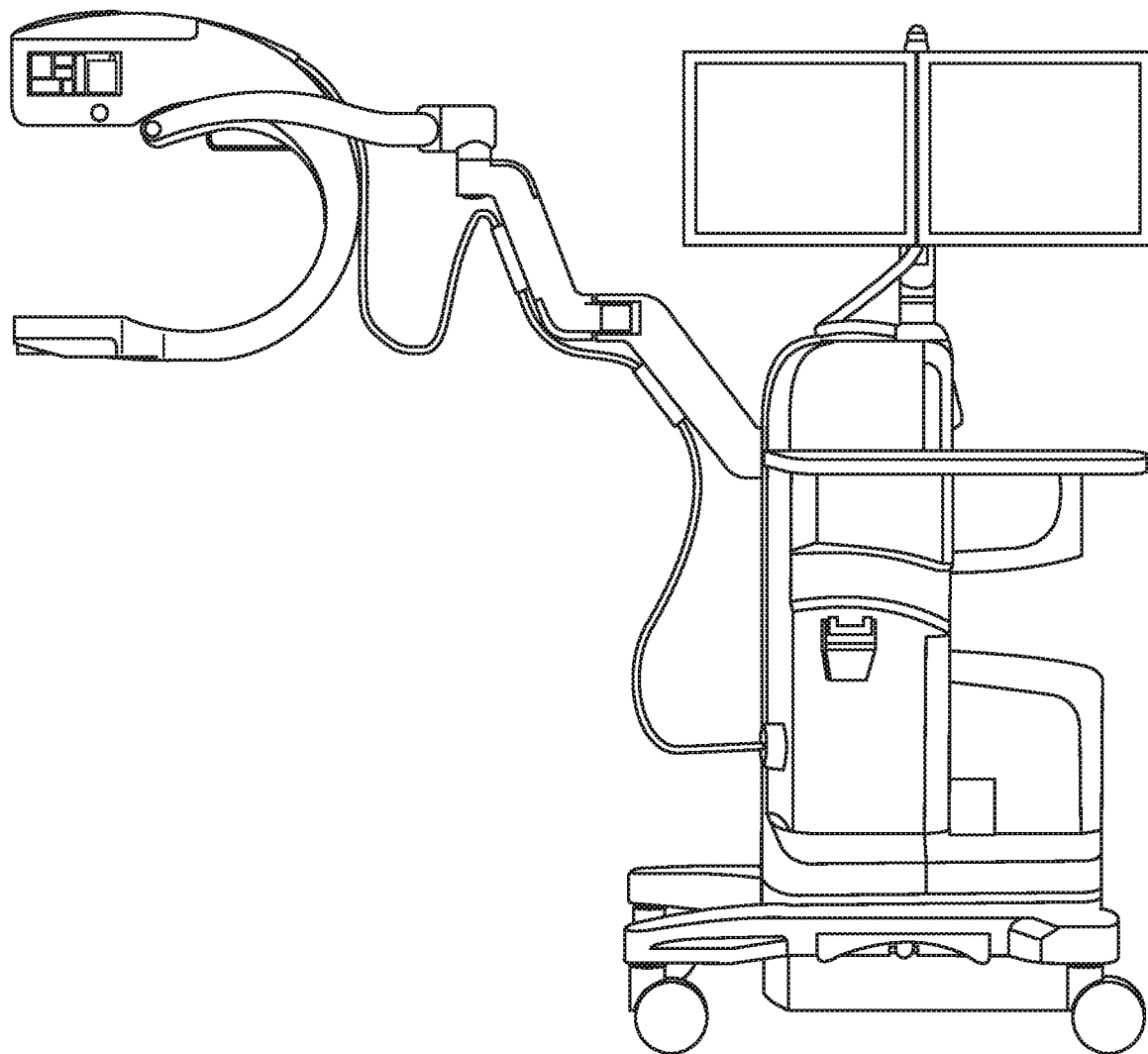
Figure 15:
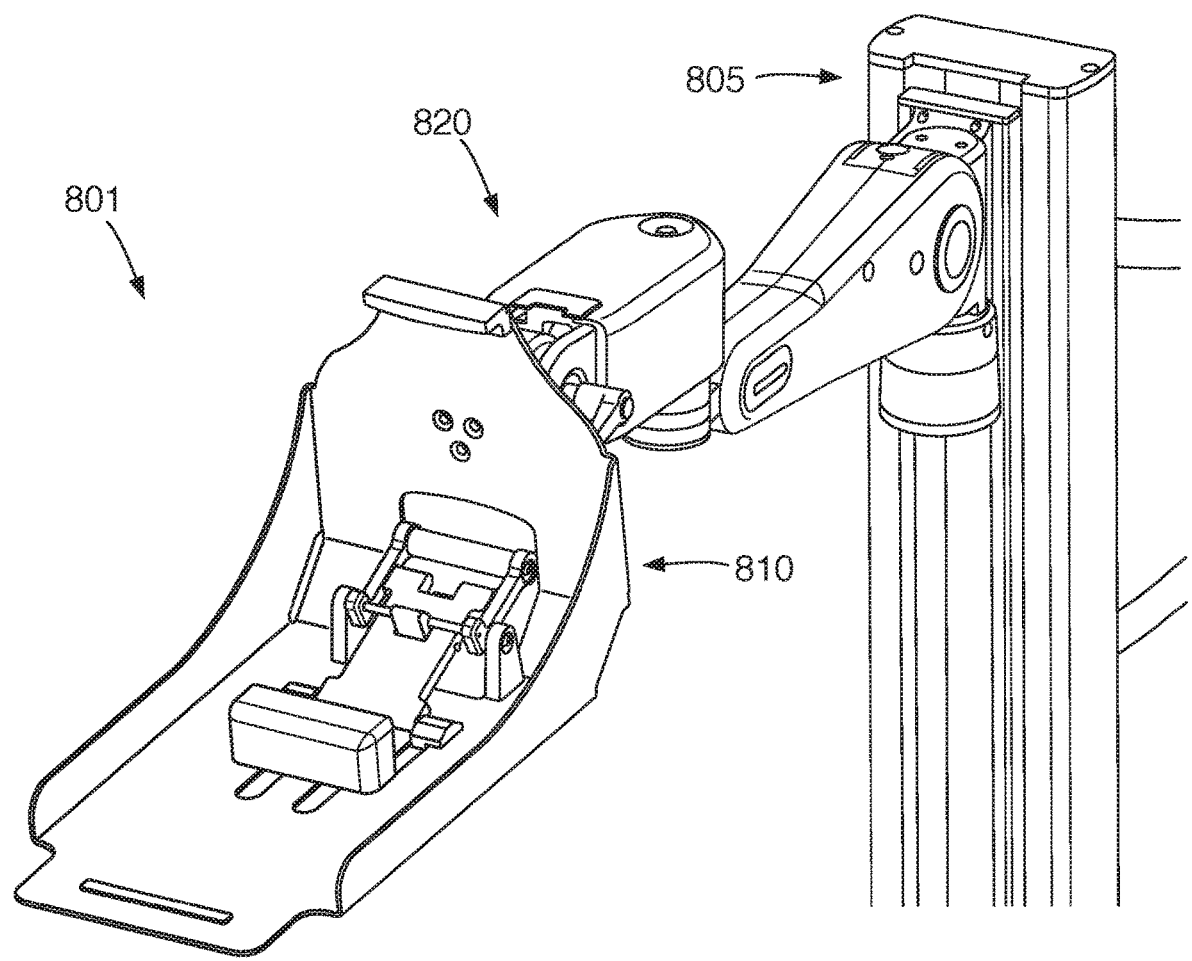
FIGS. 15-17 show other embodiments of clamping devices for attaching portable x-ray devices to a support structure.

With some conventional support structures, though, removing the portable x-ray device 100 from the support structure is either not possible, or is not an easy or quick procedure. For example, with the conventional support structure shown in FIG. 13, the x-ray device can only be removed by loosening the clamp connecting it to rest of the system, but this action does not really release the x-ray device from the x-ray system since it is still connected to the support structure by power and data cables. Thus, it cannot be easily taken to a new location and it is not truly a portable x-ray device. And with the conventional support structure shown in FIG. 14, the c-arm x-ray device can't be even removed from the support structure.

To overcome these difficulties, the portable x-ray device 100 in some embodiments can be connected to an external (or support) structure using a connecting mechanism that is secure, yet also capable of being operated by one hand while the other hand holds the portable x-ray device 100 for safety during the connection process. Using such a connecting mechanism allows an operator to quickly and easily attach (and remove) the portable x-ray device 100 from the support structure and move it freely once disconnected, making the portable x-ray device 100 truly mobile.

Figure 6:
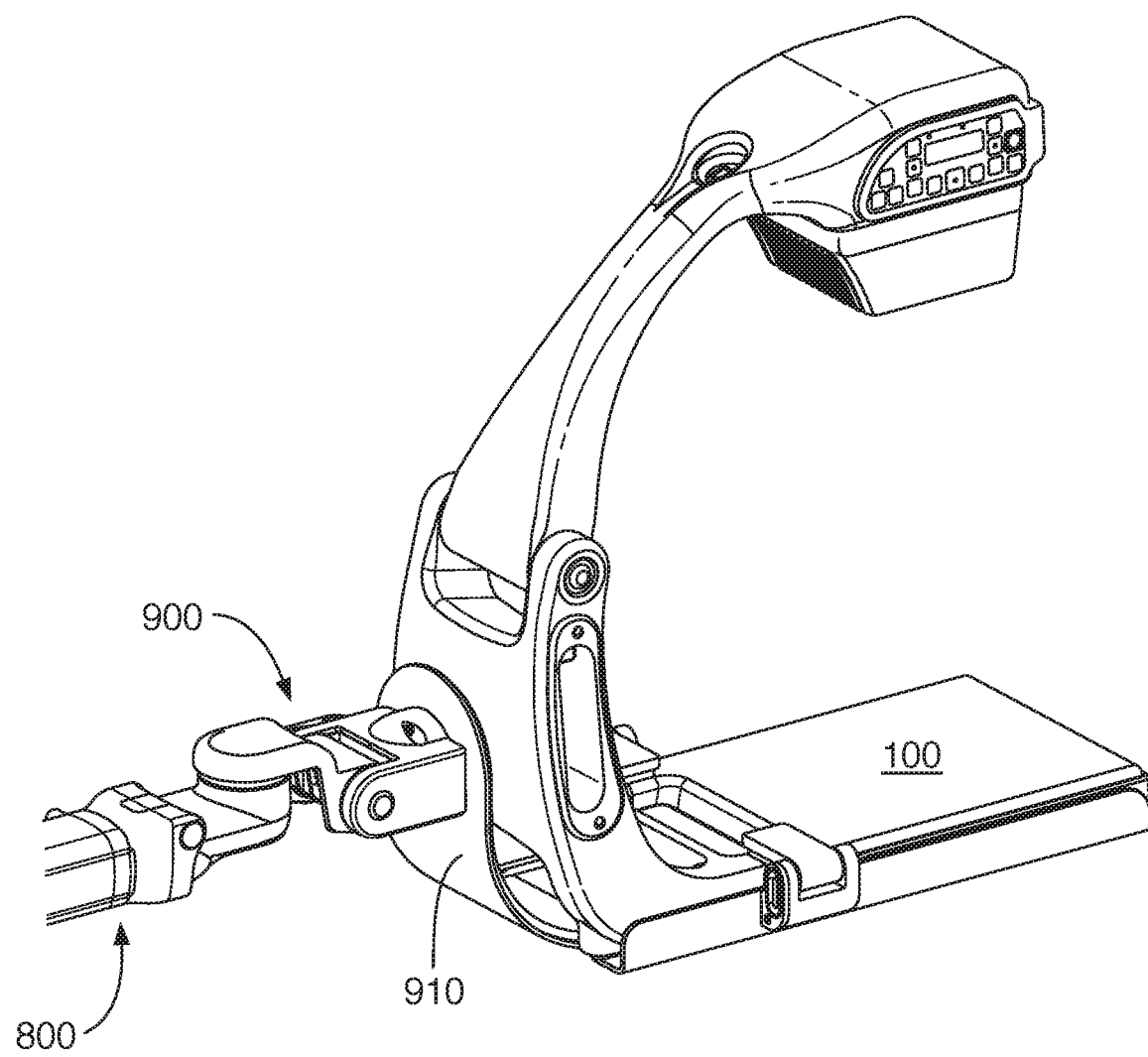
FIG. 6 illustrates some embodiments of a connecting member for attaching small, portable X-ray devices to a support structure.

In these embodiments, a connecting member 900 is used to flexibly connect the portable x-ray device 100 to any desired supporting structure. As shown in FIG. 6, an extension arm 800 of the support structure can be connected to an end of the connecting member 900. The other end of the connecting member is connected to a cradle 910 into which the portable x-ray device 100 rests. The cradle 910 is configured so that it has a surface that conforms to or meshes with the outer surface of the housing of the portable x-ray device 100 or any other desired part of the portable x-ray device 100. The portable x-ray device 100 can be attached and secured to the cradle 910 so that its position relative to the extension arm 800, and its orientation in three dimensions, is controlled by connecting member 900 during operation of the x-ray device 100. Once operation of the portable x-ray device 100 is concluded, the portable x-ray device 100 can be detached from the cradle 910.

Figure 7:
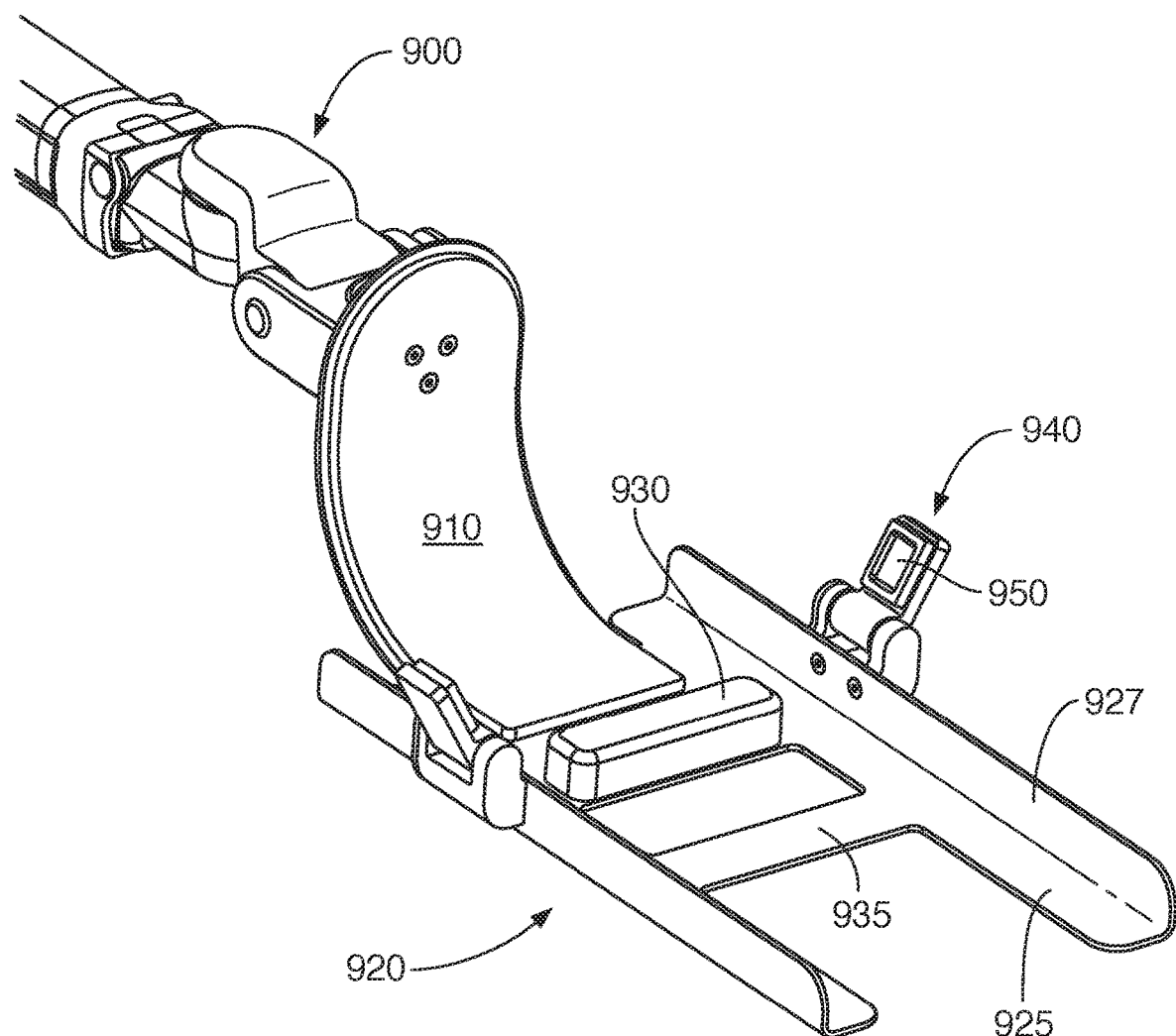
FIGS. 7-8 shows some embodiments of clamping mechanisms for attaching small, portable X-ray devices to a support structure.
Figure 8:
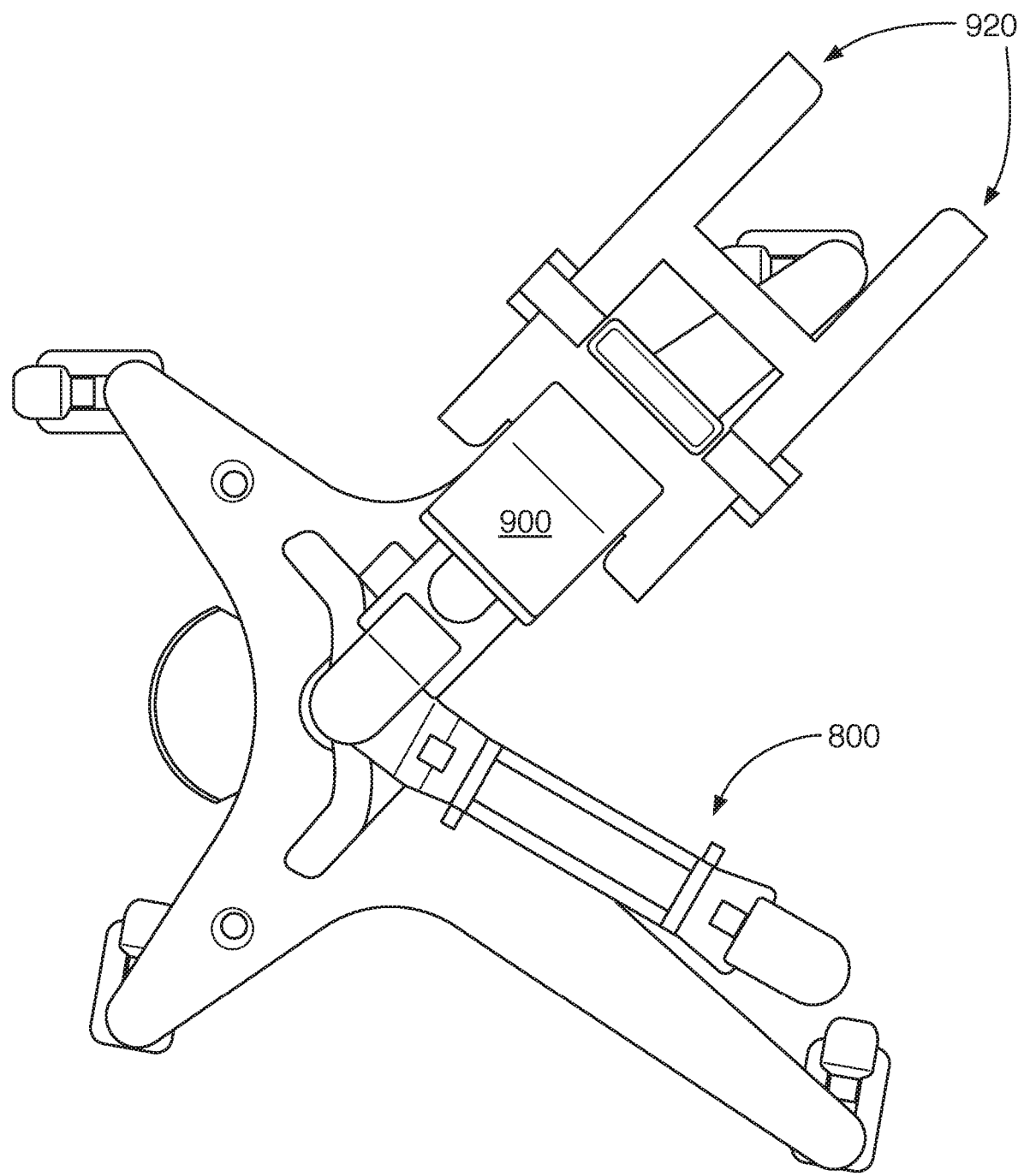

The cradle 910 also contains mounting plate(s) or support(s) 920 that are used to support the bottom of the portable x-ray device 100, as shown in the perspective view of FIG. 7 and the top view of FIG. 8. The mounting plates 920 are designed to support and contain the bottom of the portable x-ray device 100 when the portable x-ray device 100 rests on the cradle 910. So with the configuration of the portable x-ray device 100 shown in FIG. 2, the mounting plates 920 are configured to contain length members 925 with ridges 927 that are configured to extend along the length of the bottom sides of the portable x-ray device 100. The mounting plates 920 also contain width members 935 that extend between the length members 925. The width members are configured to extend along the width of the bottom of the portable x-ray device and provide rigidity to the mounting plates 920 and the entire cradle 910. While only two width members 935 are shown in FIGS. 7-8, the mounting plates 920 could have more or less than those shown in these Figures. Optionally, the mounting plates 920 could contain width members with ridges that could be located to extend along the width of the bottom sides of the portable x-ray device 100, thereby fully enclosing the bottom of the portable x-ray device.

The connecting member 900 also contains several features that can be used to secure or clamp the portable x-ray device 100 into place in the cradle 910 and the mounting plates 920. One of these features comprises insert 930 that is located near the middle of the mounting plates. The insert 930 extends upwards from the mounting plates 920 and is configured with a size and shape that mates with an opening 175 in the portable x-ray device 100. The mating of an opening 175 in the portable x-ray device 100 as depicted that accepts the insert 930 as depicted provides immediate registration and location of the portable x-ray device 100 accurately on the cradle 910. This is helpful for a quick attachment and/or quick release of the portable x-ray device 100. Without such a registration feature, the medical personnel operating the portable x-ray device 100 would spend precious time adjusting and positioning the portable x-ray device 100 on the cradle 910 instead of on the needed part of the medical procedure. And with such a registration feature, the registration or positioning is automatic.

In other embodiments, the registration insert 930 and matching opening 175 could be rectangular in shape, or circular, or oval, or any other shape that allows the combination of the opening 175 and the insert 930 together. As well, the height of the registration insert 130 (and the corresponding depth of the opening 175) can be modified from what is shown in the Figures. And while a single registration feature is shown in the Figures, multiple registration features with the same or different sizes and shapes (along with matching openings in the portable x-ray device 100) can be used. In other embodiments, the registration insert could be located on the portable x-ray device 100 and a matching opening could be located on the mounting plate(s).

Another securing feature in cradle 910 is the clamps 940. The clamps 940 are located on the ridges (or side stiffeners) 927 of the length members 925 of the mounting plates 920 so that they are situated on opposing sides of the bottom of the portable x-ray device 100. The clamps 940 can remain open when not used and closed on the portable x-ray device 100 when needed. Alternatively, the clamps 940 could be closed when not in use at the expense of an additional motion or moment of time to open them before x-ray device 100 could be mounted on the cradle 910. Examples of this opening and closing action are shown in FIGS. 9-12 where the clamps 940 are in an open position in FIG. 9, partially closed positions in FIGS. 10-11, and in a completely closed position in FIG. 12 to secure the portable x-ray device 100 to the cradle 910 and mounting plates 920.

The clamps 940 can be configured to meet multiple requirements. One requirement is to have at least two independent failure points in securing the portable x-ray device 100 to the cradle 910. This functionality can be accomplished in part by requiring that each of the clamps 940 have a separate release button, lever, or other mechanism that releases the clamp 940 from the portable x-ray device 100. Thus, if one of the clamps 940 is accidently opened or were to fail, the other clamp, combined with the physical registration or constraining action of the insert 930 in the opening 175, would ensure that the portable x-ray device 100 cannot slip or fall from the cradle 910, even if it is no longer snuggly or firmly fixed in the cradle 910.

This functionality demonstrates another benefit obtained by using the insert 930. Not only does insert 930 register the portable x-ray device 100 as described herein, but it also acts to help secure the x-ray device 100 in the cradle 910 against accidental release. In order to accomplish this function, the insert 930 should mesh snuggly and reasonably tight within the opening 175. But if the fit is too tight, then the portable X-ray device 100 will be difficult to mount or remove from the cradle 910. Yet if the fit is too loose, the insert 930 may not act appropriately as part of the secure mounting system described herein. So a balanced fit has to be used.

In other embodiments, additional clamps 940 could be used on the mounting plates 920 so that the cradle 910 contains 3, 4 or even more clamps. Additional clamps could be positioned on the bottom of cradle 910 to clamp the portable x-ray device 100 by securing them to the length members 925 of the cradle to press the C-arm against the mounting plates 920, or by mounting them in other ways. However, the use of more than 2 clamps may not be needed in some embodiments since additional clamps will complicate the mounting or removal of the portable x-ray device 100 to the cradle 910 without providing additional security or physical stability beyond that provided by just using two clamps.

In other configurations, the clamps 940 and the portable x-ray device 100 can be provided with matching features to help the clamping function. For example, the clamps 940 depicted in FIG. 7 contain extensions 950 that are flexible and compress when the clamps 940 are secured on the housing of the portable x-ray device 100 in order to provide some positive pressure on the x-ray device 100 to keep it firmly seated. But the extensions 950 could also be configured to be inflexible and mated to matching indentations in the portable x-ray device (not shown).

The clamps 940 can be actuated or applied to the portable x-ray device 100 in any number of ways. It is possible for the clamps 940 to be spring loaded such that they snap shut on the x-ray device 100 when actuated by a button, a lever, or some other feature. Alternatively, the clamps 940 could be actuated by a clamping lever (not shown) that would work within the clamping mechanism to close the clamps and apply pressure to secure the x-ray device 100. In other embodiments, the clamps 940 could be designed to contain an internal ratchet mechanism (or similar functionality) that is light enough in action that the clamps can be pressed or squeezed closed using one hand and the pressure of the fingers and palms and retain the clamps 940 in the closed position automatically, retaining the pressure against the portable x-ray device 100 that was initially imparted by hand. This ratchet mechanism can also be configured to only partially open when initially released by the operator using the button, lever, or other actuator, so that the C-arm of the portable x-ray device 100 can't fall out of the cradle 910 until the clamp 940 has been fully released with a second activation of the release mechanism.

Figure 9:
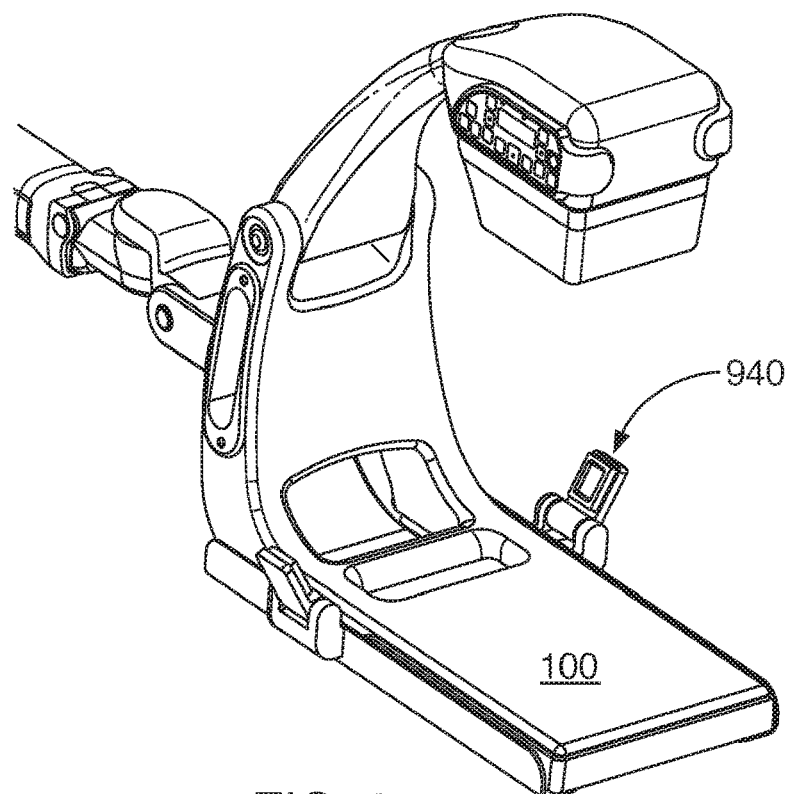
FIGS. 9-12 shows some embodiments of opened and closed clamping mechanisms for attaching small, portable X-ray devices to a support structure.
Figure 10:
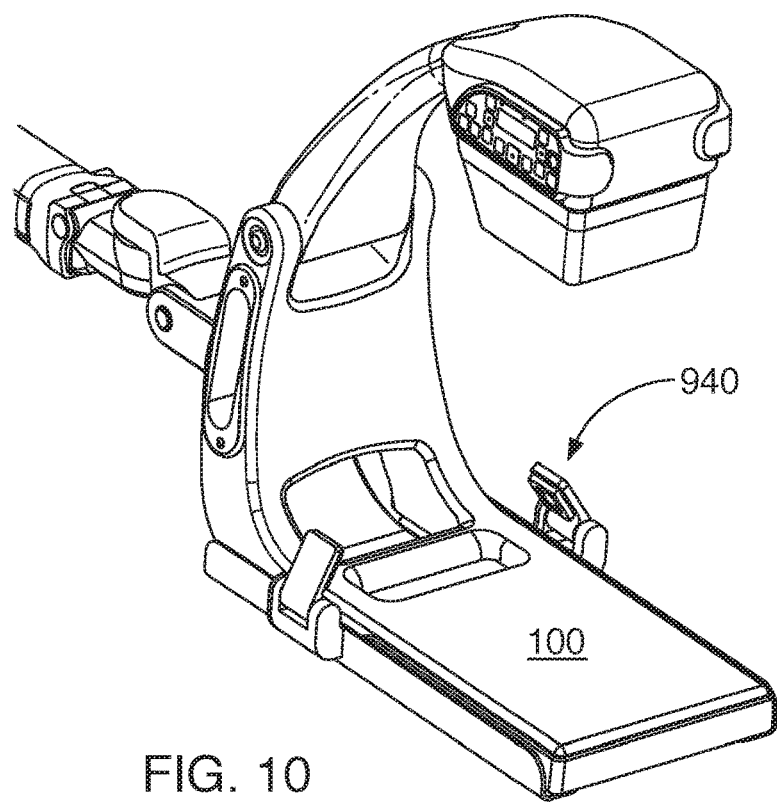
Figure 11:
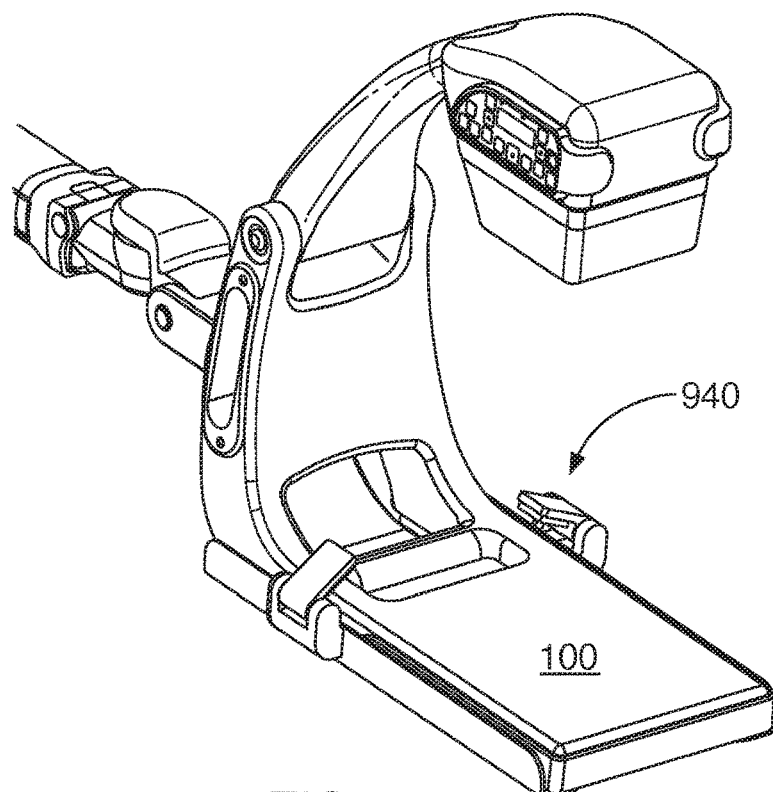
Figure 12:
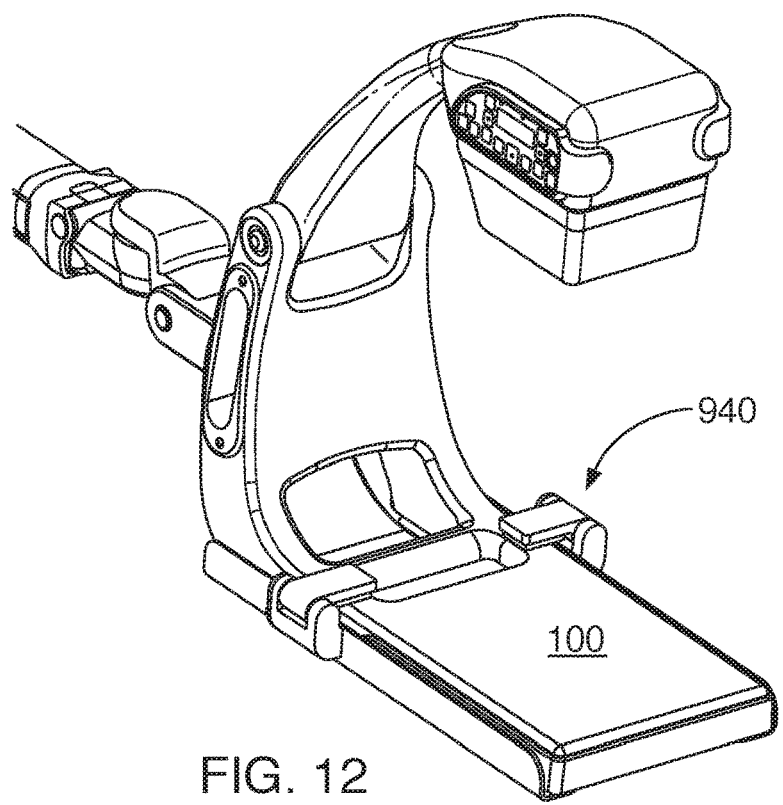

The portable x-ray device 100 can quickly and easily be attached and removed from the cradle 910 and mounting plates 920 using a single hand by an average sized operator in the following manner. When the clamps 940 are in the open position shown in FIG. 7, the portable x-ray device can be carried by hand and placed onto the cradle and mounting plates so that the insert 930 fits within the opening 175, as shown in FIG. 9. The clamps 940 can then be closed by an operator, as shown in FIGS. 10-12. The portable x-ray device 100 can then be operated to take an x-ray image of the patient without the medical personnel constantly holding the portable x-ray device 100. When needed, the clamps 940 can be opened by pressing the button or otherwise activating the release mechanism, and then the portable x-ray device 100 can be easily lifted off the cradle/mounting plates using only a single hand by the average person.

When the portable x-ray device 100 is attached to the cradle and mounting plates, it can be used in imaging procedures of a patient. Some of those imaging procedures can be performed during a surgical procedure where a sterile field needs to be maintained. One manner of maintaining a sterile field is by using a sterile bag around the portable x-ray device 100. To keep the sterile field, the clamps 940 and the insert 930 must be configured so that such a sterile bag is not punctured when the clamps are closed.

In some configurations, the connecting member 900 containing the cradle 910 is connected to a supporting device, such as a support stand. The support stand that is attached to and supports the cradle 910 through connection member 900 will intentionally or may accidentally be brought close to the patient. To maintain a sterile field near the patient, a sterile bag can be placed over the support stand and the cradle 910 before the portable x-ray device 100, in a separate sterile bag, is mounted or placed in the cradle 910. In other words, two sterile bags can be used: a first sterile bag covering the cradle 910, the connecting member 900, and the rest of the support stand as appropriate, and a second sterile bag around the portable x-ray device 100 itself. Such a configuration will allow the portable x-ray device 100 to be maintained sterile, while simultaneously allowing for the rapid and easy removal of the portable x-ray device 100 during the medical procedure.

This requirement of using two sterile bags in these embodiments can introduce additional constraints on the insert 930, the clamps 940, and even on the mounting plates 920, as well as other components of the portable x-ray device 100, especially the opening 175. The first constraint is that all of these features, whether part of the cradle 910, the x-ray device 100, or the clamps 940, must be designed with rounded surfaces, chamfers, or other means to smooth corners and edges so that the sterile bags cannot be caught and torn, or punctured. In some configurations, the corners, edges, chamfers, and other rounding of features have a minimum radius no smaller than about 0.5 mm, with about 1.0 mm or about 2.0 mm as a more practical minimum since the sharper the corner (i.e., the smaller the radius), the more easily a polymer film sterile bag can be torn or inadvertently penetrated. The minimum corner radius also depends on the shape of the feature. If, for example, the feature is a flat plate or surface that is only 2 mm or 3 mm thick, the corner radius will essentially become a circle with a radius of one half the thickness of the plate. This configuration would be the case for many handles, levers, and other such features.

It is also desirable that all surfaces must have some significant area so that there is no feature (including features such as handles, clamping levers, and similar devices) that is capable of, or likely to, puncture the sterile bag if the bag is stretched across the physical feature. So handles, clamping levers, and similar devices can be designed or angled to lie close to the adjacent surface in order to avoid any features that poke out from the over-all device at large angles of about 60 degrees, about 70 degrees, about 80 degrees, or about 90 degrees. Handles, clamping levers, and similar devices should also have a rounded end with a radius of at least about 2 mm, about 3 mm, about 4 mm, or even about 5 mm in order to avoid punctures of the sterile bag polymer sheet. Additionally, any hinges, such as in the clamps 940 must be designed to ensure that a thin plastic sheet or membrane from a sterile bag cannot be caught, torn, or punctured by the operation of the clamps 940.

An additional constraint is that the clamp 940 must be able to accommodate the variations in the clamping conditions caused by the absence of any sterile bags, or the presence of 1, 2, 3 4, 5, or even more layers of plastic between the x-ray device 100 and the cradle 910, clamps 940, and/or resilient pads 950. These intervening layers can be caused by sterile drapes on the support stand and/or the portable x-ray device 100 since one or more folds in the sterile bag material might be captured between the x-ray device 100 and the cradle 910, clamps 940, and/or resilient pads 950. These folds can be introduced because sterile drapes are designed to be somewhat loose and baggy to allow for the quick application of the sterile bag over the component to be rendered (or maintained) sterile. This looseness is often dealt with by gathering some folds together at various locations of the component that is covered by the sterile bag.

Therefore, the clamps 940 and the resilient pads 950 need to be able to accommodate a variety of clamping conditions. For example, if the sterile bag material is 5 thousandths of an inch (i.e., 5 mils or 0.127 mm) thick, the clamping mechanism needs to be able to successfully and adequately clamp the portable x-ray device 100 with the variation in the total effective material thickness ranging from 5 mils, to 10 mils, 15 mils, 20 mils, 25 mils, 30 mils, or even more. Converting to millimeters, the equivalent thickness could vary by about 0.1 mm, to 0.2 mm, 0.3 mm, 0.4 mm, 0.5 mm, up to 0.6 mm, 0.7 mm, or even more. The resilience that the clamping mechanism requires to deal with such a broad variation in thickness could be designed into the pad 950 by using rubber, foam, foam rubber, or similar material. It also could be designed into a combination of the pad 950, the clamp 940 and its mechanism, and/or even into the design of the cradle 910 by incorporating a resilient foam, or rubber, or other such resilient material into the cradle 910 by placing it on the length members 925 and width members 935.

Other embodiments of the clamping devices that can be used to secure the x-ray device to the support structure are shown in FIGS. 15-22. In these embodiments, the clamping devices are much simpler and more secure than the clamping mechanisms illustrated in FIGS. 6-12. As shown in the embodiments depicted in FIG. 15, the clamping device 801 contains a cradle 810 configured substantially similar to cradle 910 so that it mates with the surface of a portion of the x-ray device 100. Cradle 810 contains a connecting member 820 that is used to connect the clamping device 801 to an external support structure 805. The connecting member 820 counterbalances the roll, pitch, and yaw motions of the x-ray device 100.

Figure 16:
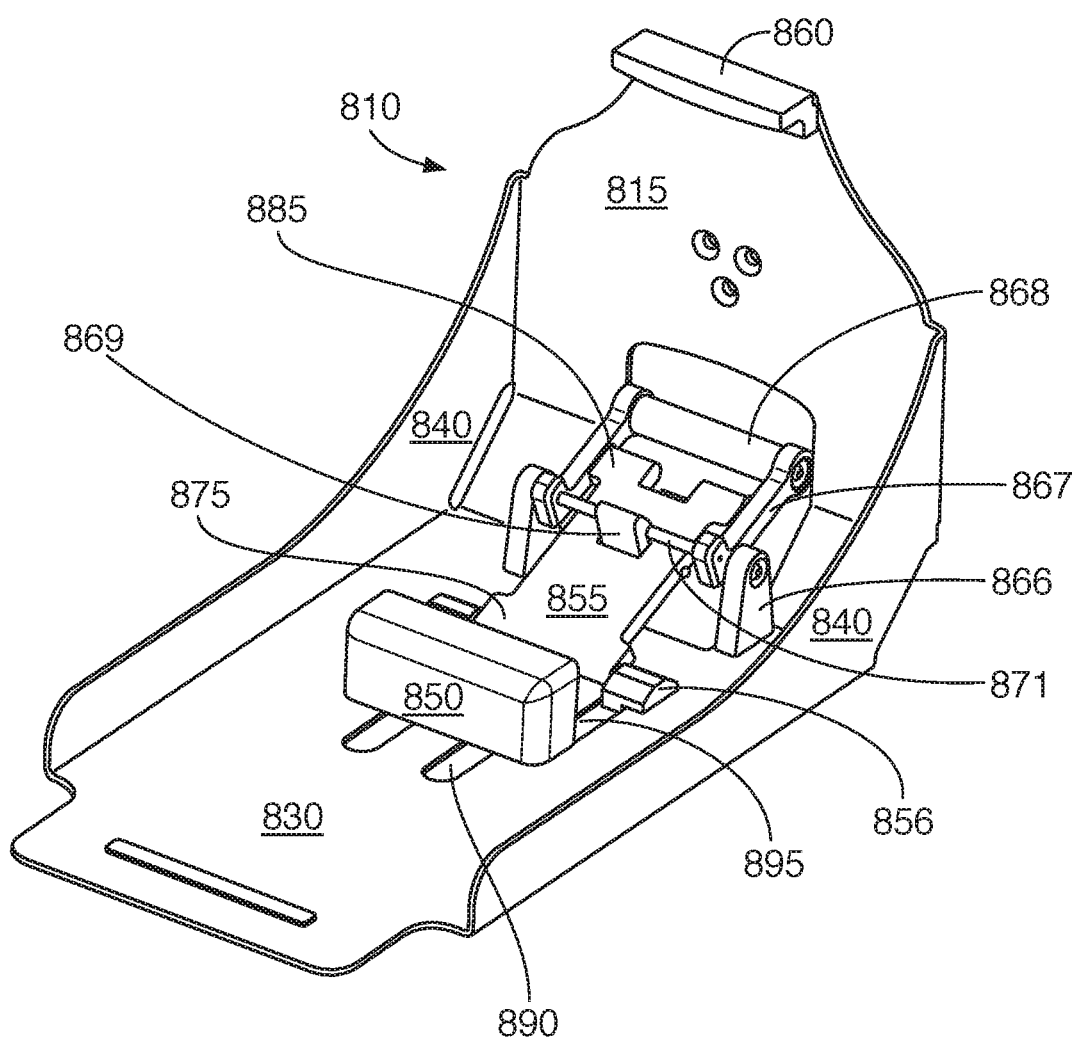

Unlike cradle 910, though, the cradle 810 contains a constraining member 860 close to one end of the cradle 810, as shown in FIG. 16. The constraining member (or restraint) 860 is configured to fit within upper opening 195 of the x-ray device 100 that is located just below the hinge 165 of the x-ray device 100, as shown in FIG. 2. The constraining member 860 helps support and restrain the x-ray device 100 when it is connected to the cradle 810. In other embodiments, a constraining member similar to constraining member 860 could also be used with the configurations of the clamping mechanism that work with cradle 910. The constraining member 860 helps retention of the x-arm device 100 in the cradle 810 when the x-ray device 100 is rotated upside down, or is moved to a position where the C-arm device would otherwise fall out of the cradle 810 without the constraining member 860.

Instead of mounting plates 920, though, the cradle 810 contains a single mounting plate 830 as shown in FIG. 16. This mounting plate 830 is configured to mate with an outer surface of the bottom of the x-ray device 100, in a manner similar to the mounting plate 920 shown in FIG. 7. However, there are several changes in mounting plate 830 that improve upon the mounting plate 920. These improvements are found in the side members 840 which continue through to and are attached or formed as part of the back wall/attachment plate 815 (or upper section 815 of cradle 810). The side members 840 provide a similar function to the side members 927 shown in FIG. 7 in constraining and positioning the x-ray device 100 in the cradle 910 and mounting plates 920. The differences in the depth of the side members 840 in comparison to the side members 927 depicted in FIG. 7, and their continuation into the attachment plate 815, provides for additional stiffness and rigidity in the mounting plate 830 and the over-all cradle 810, thereby providing a more stable mounting for the x-ray device 100 with less susceptibility to vibration, bouncing, or oscillatory movement of the x-ray device 100 when mounted on the extension arm of the support structure as it is moved or positioned by the user.

For reasons of economy in manufacturing, as well as the improved appearance of smooth bends in a metal plate as opposed to the appearance of welds, soldering, or other means of fastening two metal pieces together, the mounting plate 830 can be constructed of a single sheet metal piece as much as possible. Mounting plate 830 may also include cutouts or holes similar to those shown in mounting plate 920 in FIG. 7, as well as cutouts in the side members 840 in order to reduce the over-all weight, provided that the stiffness and the support points necessary to achieve a stable mount for the X-ray device 100 are maintained.

Figure 17:
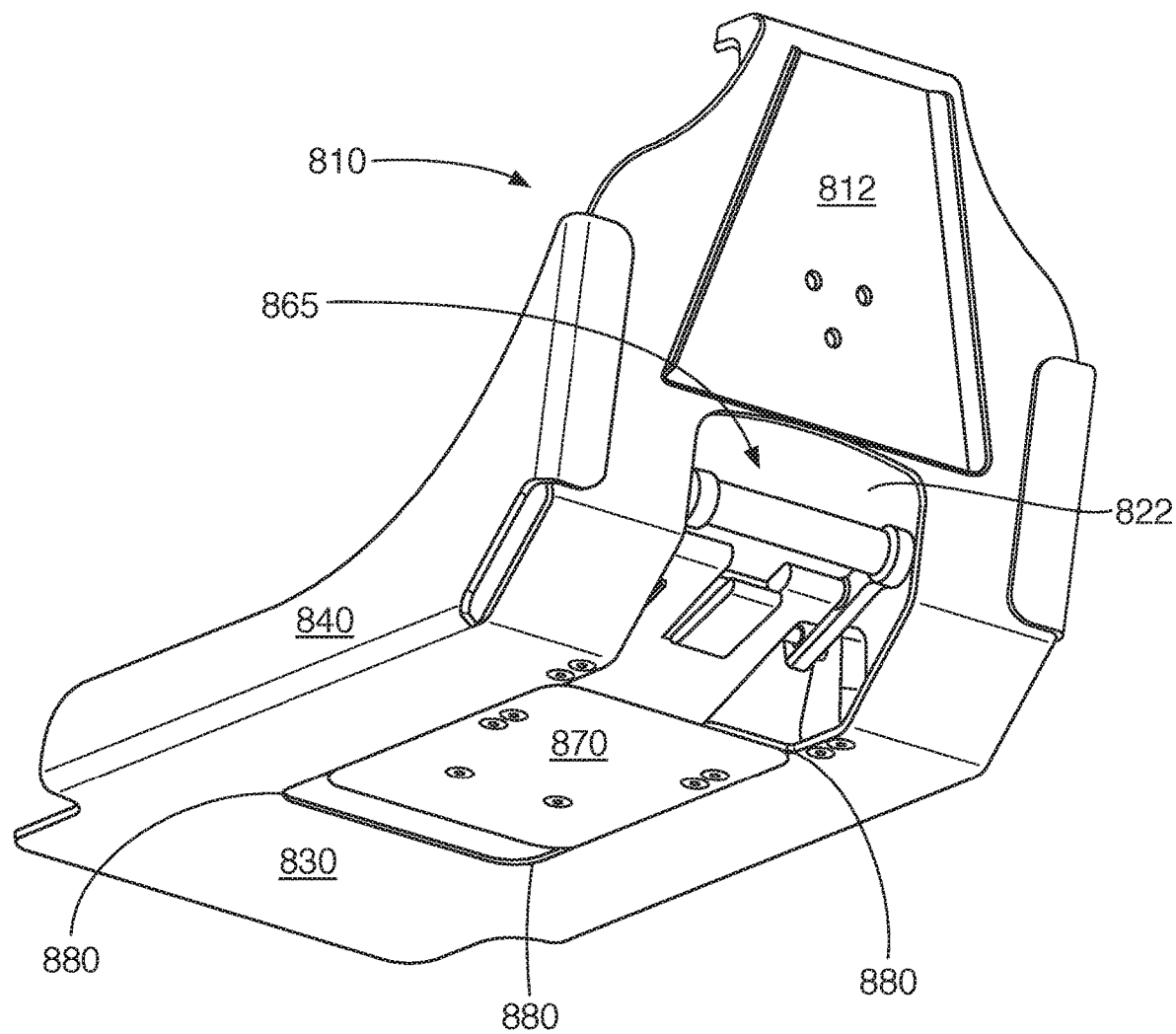

The clamping device 801 also contains a registration device (or insert) 850. The insert 850 is configured substantially similar to the insert 930 so that it mates with opening 175 in the bottom of the x-ray device 100. The insert 850 is also mounted to the cradle 810 so that the insert 850 can slide laterally along the length of the mounting plate 830 due to connections that pass through the openings 890 to an underlying sliding or moving mechanism. This functionality is useful when mounting (and removing) the x-ray device 100 to (and from) the cradle 810. In some configurations, the insert 850 can be connected to the cradle 810 using a sliding plate 870 located on the bottom side of the cradle 810, as shown in FIG. 17. The sliding plate 870 can move laterally on the bottom of the cradle 810 within a recessed region 880 that has been cut, stamped, pressed, or otherwise formed into the bottom of mounting plate 830. Alternatively, the sliding plate 870 could be constrained by ridges or other guidance means formed into the bottom of the mounting plate 830 for the purpose of guiding the sliding plate 870 as it moves in one direction, but is constrained in the other direction. The lateral movement of the insert 850 is also constrained by openings 890 in the mounting plate 830 which limit the movement of the insert 850, as shown in FIG. 16.

The clamping device 800 also contains a connecting member 855. The connecting member 855 is connected at a first end 875 to sliding connectors 856 which are situated in openings 895 and fastened to the sliding plate 870 on the underside of mounting plate 830. The sliding connectors 856 (and therefore the first end 875 of the connecting member 855) can move laterally along the mounting plate 830 within openings 895 while being connected to sliding plate 870. The second end 885 of the connecting member 855 is connected to an attachment device 865. Such a configuration allows the connecting member 855 to be contained within opening 185 of the x-ray device 100 while moving at the same time within the cradle 810.

The clamping device 801 contains an attachment device 865 that can be accessed or operated through the opening 822 in the cradle 810 and through the opening 185 of the x-ray device 100. In the configurations shown in FIGS. 16 and 17, the attachment device 865 is shown in a mounted or locked position that would be used when X-ray device 100 is mounted on the cradle 810. The attachment device 865 comprises support members 866 that are connected to a pivot arm 867. One end of the pivot arm is connected to handle 868 and the other end of the pivot arm is connected to pivot bar 871. A locking arm 869 is latched onto pivot bar 871 to retain the attachment device 865 in a locked position.

Figure 18A:
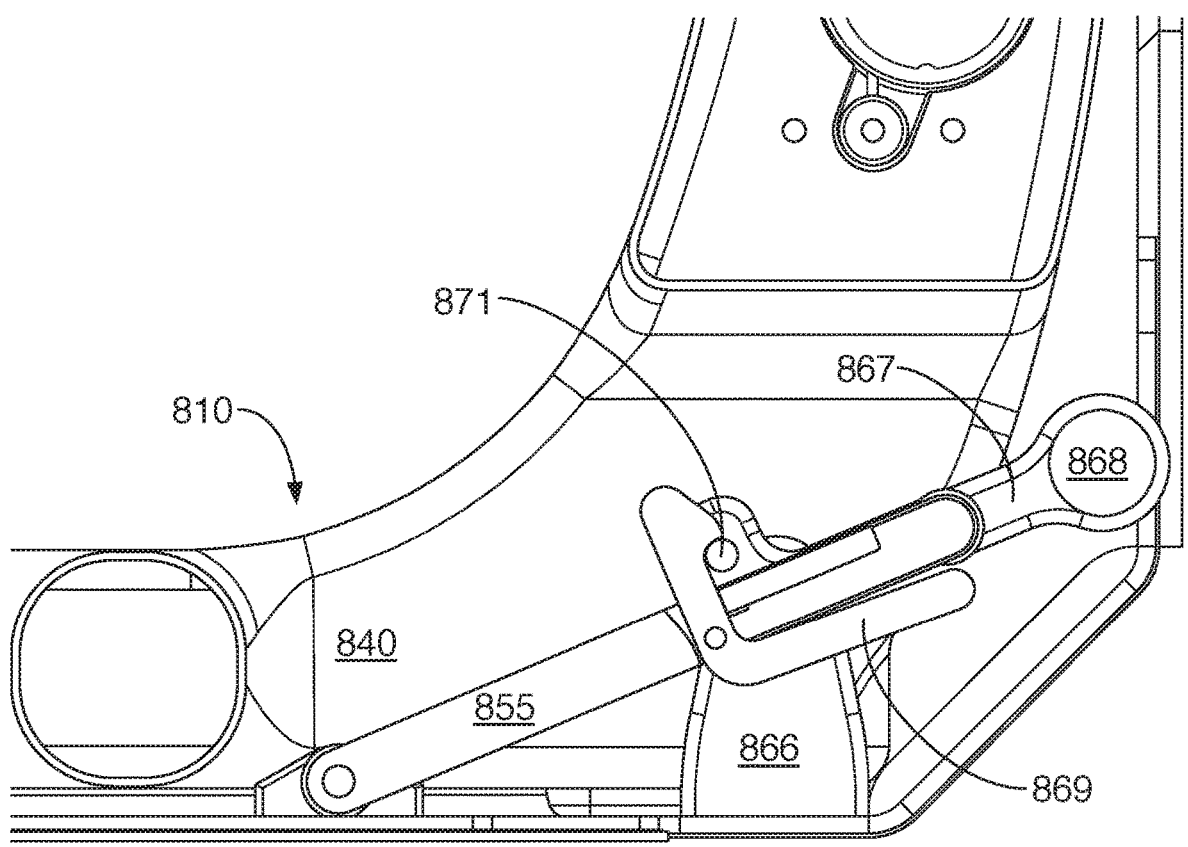
FIGS. 18A-18C show some side views of the clamping devices for attaching portable x-ray devices to a support structure.
Figure 18B:
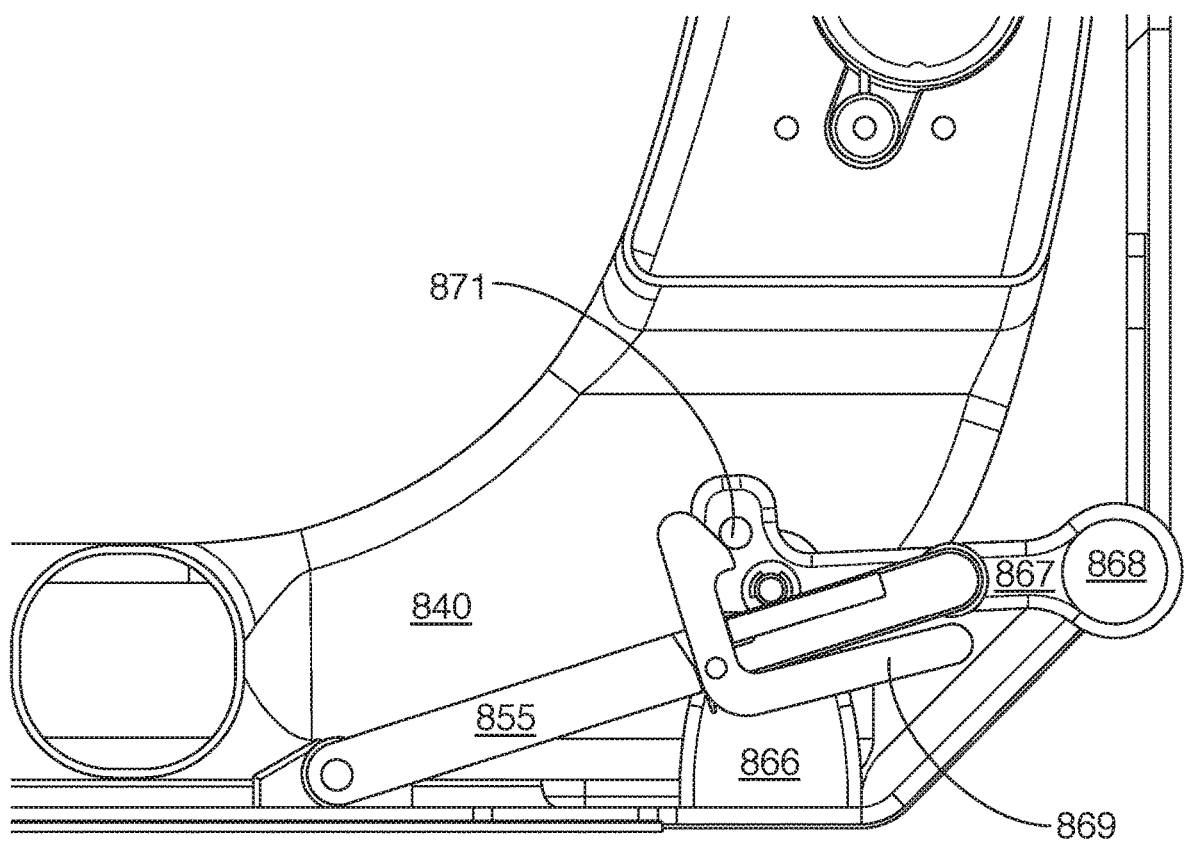
Figure 18C:
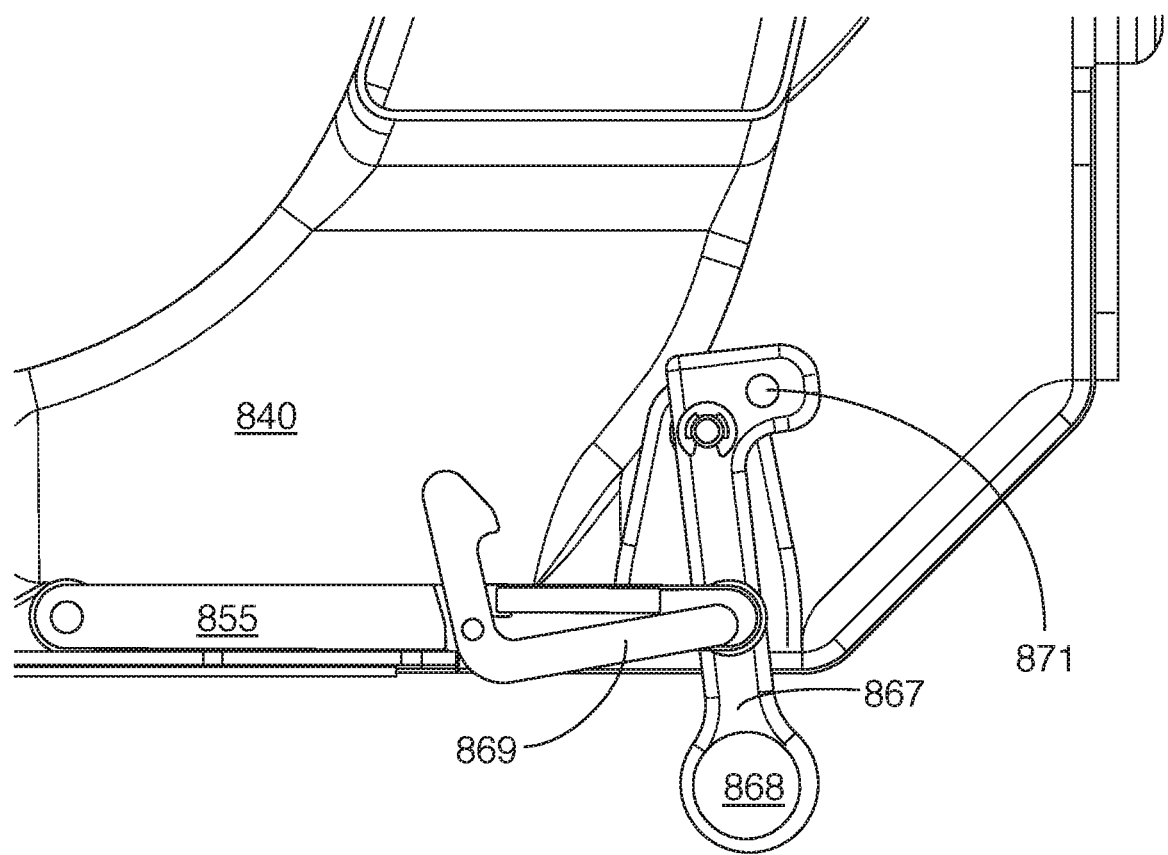

This attachment device 865 is used to move the x-ray device 100 laterally along the cradle 810 after the x-ray device 100 has been placed on the registration insert 850. This lateral motion will pull the x-ray device 100 back toward the upper cradle 815 and cause the constraining member 860 to capture the x-ray device 100 securely in place once attachment device 865 reaches a locking position. Conversely, attachment device 865 can be moved to an unlocked position causing the x-ray device 100 to slide away from constraining member/restraint 860 to allow the x-ray device 100 to be removed from the cradle 810 once it reaches the unlocked (or released) position. A locking position for the attachment device 865 is shown in FIG. 18A, an intermediate position is shown in FIG. 18B, and an unlocked position for the attachment device 865 is shown in FIG. 18C. In the locking position, the lock arm 869 is latched onto the pivot bar 871. To start the release process, the handle 868 can be pulled toward the position in FIG. 18B, which unlatches the locking arm 869 from the pivot bar 871, and also beings to move the connecting member 855 because it is fastened to the pivot arm 867. To complete the release process, the handle 868 can be moved into the position shown in FIG. 18C. This action forces the connecting member 855 to move laterally away from the support members 866, also forcing the registration insert 850 to move laterally in the same direction since both the insert 850 and the connecting member 855 are both connected to sliding plate 870.

Figure 19:
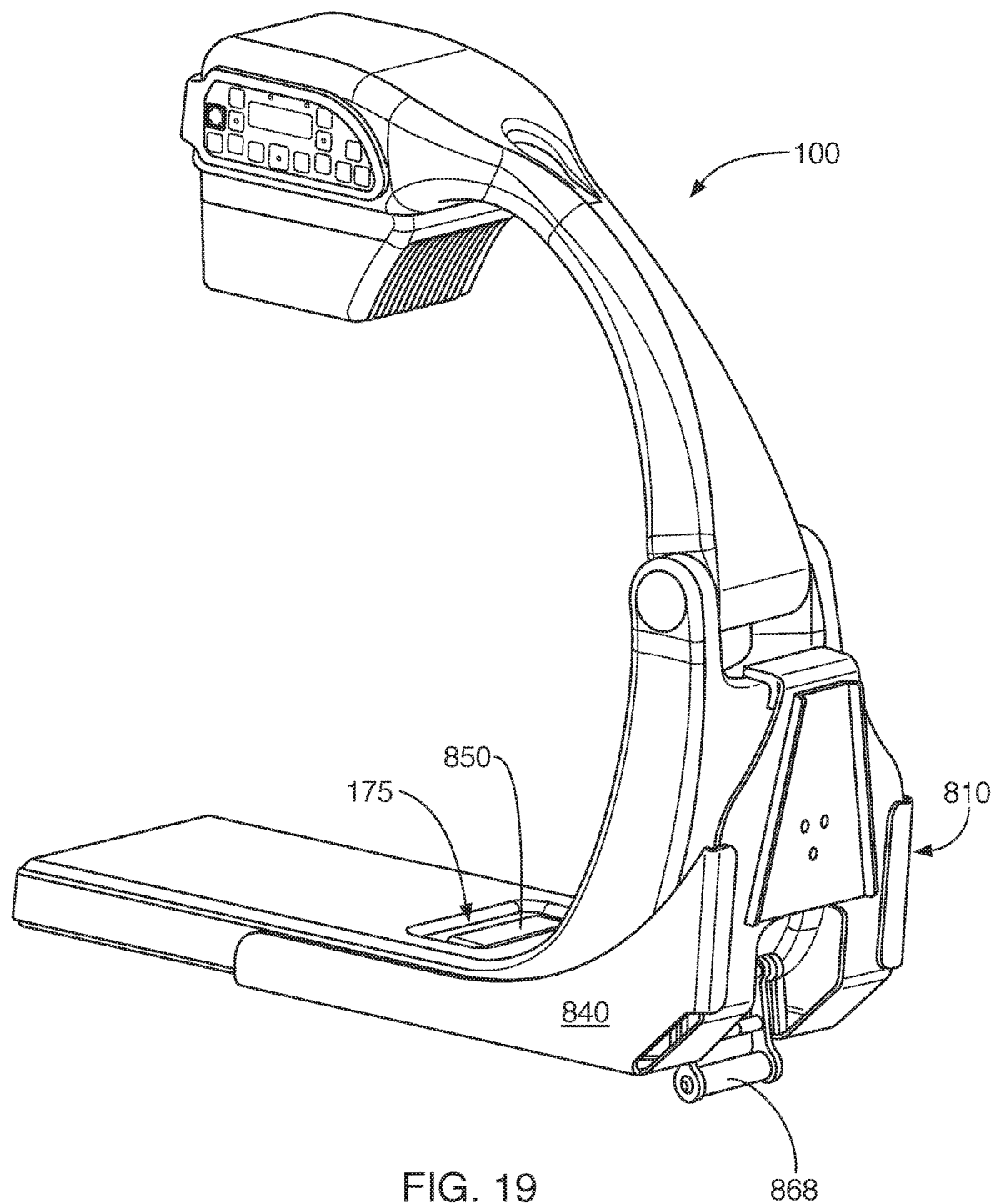
FIGS. 19-22 show methods for using the clamping devices to secure portable X-ray devices to a support structure.
Figure 20:
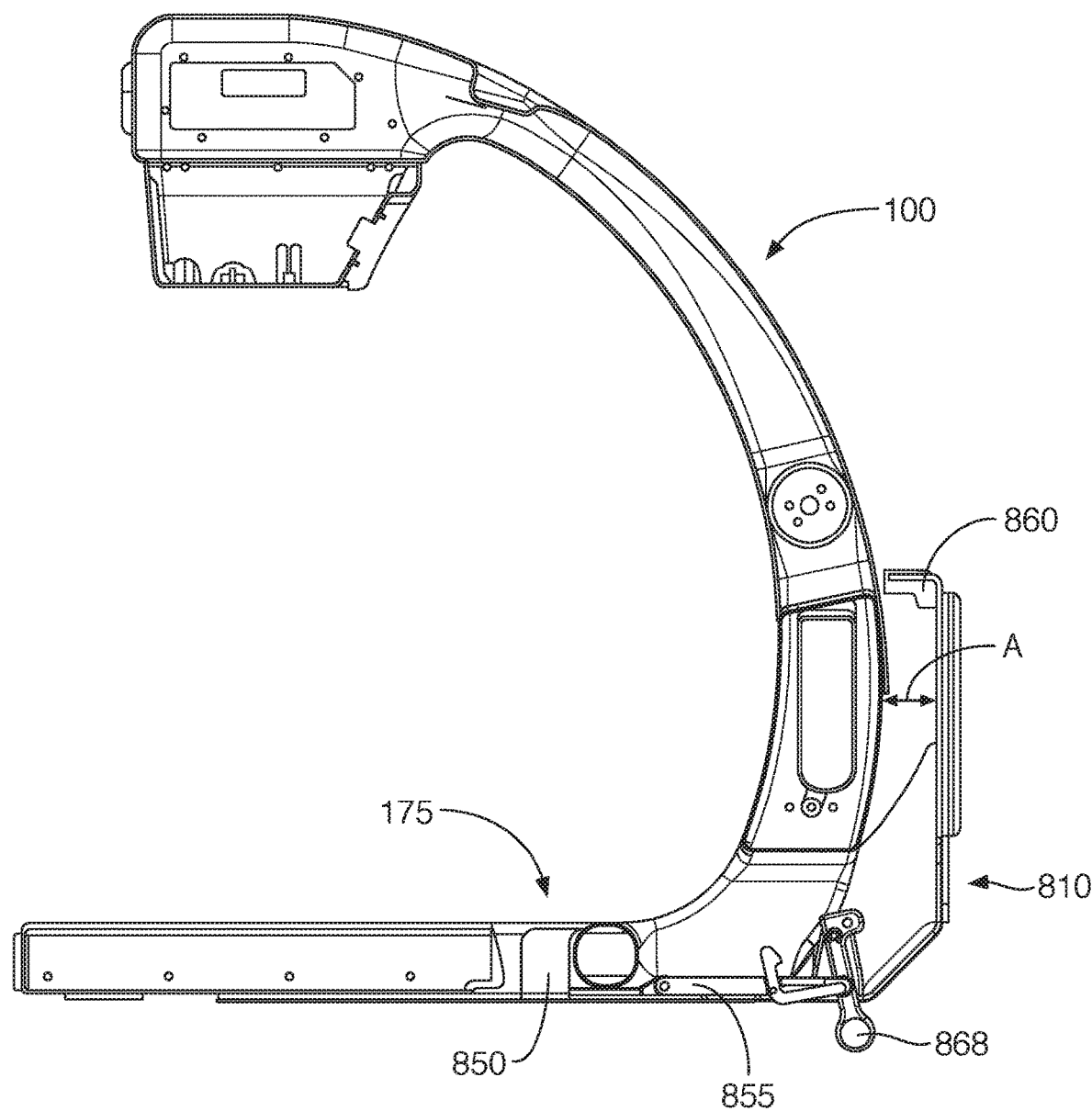

In these embodiments, the x-ray device 100 can be attached or mounted to the external support structure using the clamping device 801 using the process illustrated in FIGS. 19-22. As shown in FIGS. 19-20, the x-ray device 100 is placed on the cradle 810 so that the insert 850 mates with the opening 175 of the x-ray device 100. In this position, the attachment device 865 fits within the open section 185 of the x-ray device 100 and the upper section 815 of the cradle 810 is spaced slightly away from the back side (shown by distance A in FIG. 20) of the x-ray device 100 just below the hinge 165. In this position, the handle 868 of the clamping device 800 is in an unlocked position and the bottom of the x-ray device 100 abuts, and is supported by, the mounting plate 830 of the cradle 810. But the upper section 815 of the cradle 815 does not abut the portable x-ray device 100 since it is separated by the distance A.

Figure 21:
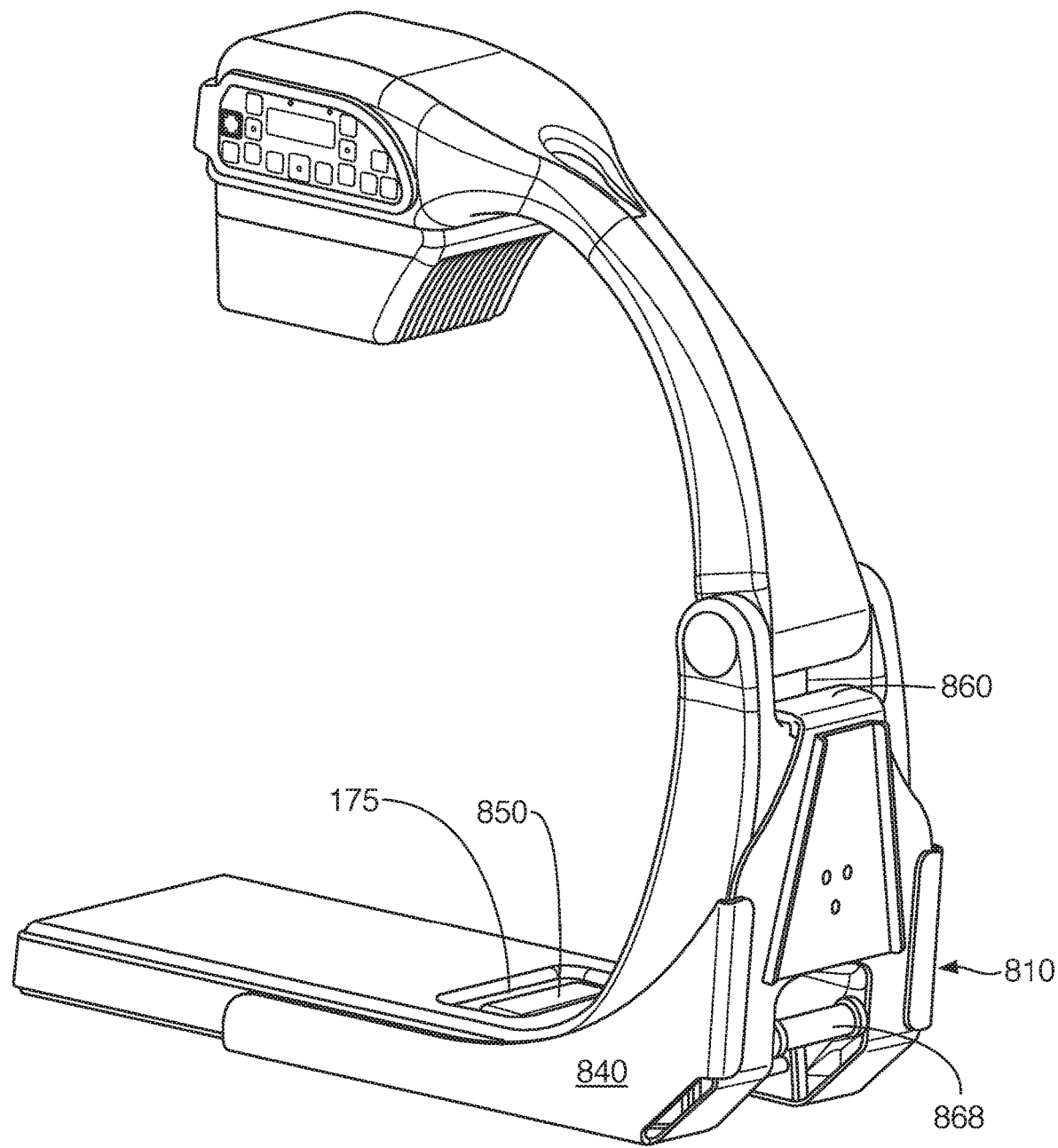
Figure 22:
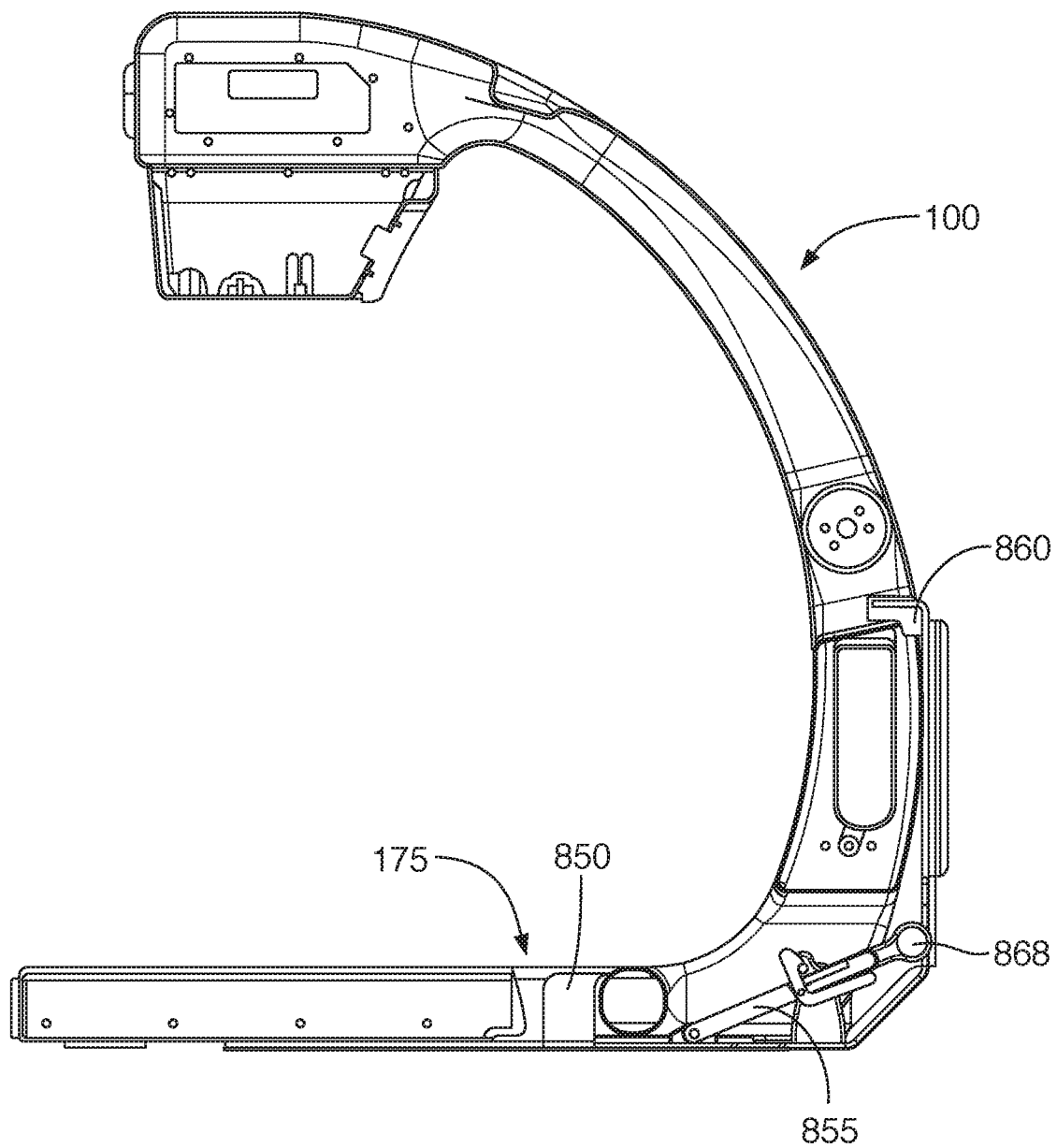

To attach and lock the x-ray device 100 to the cradle 810 (and therefore the external support structure 805), the handle 868 is moved by the operator to a locked position as shown in FIGS. 21-22. This action causes the attachment device 865 to move from the position shown in FIG. 18C, to the position shown in FIG. 18B, and finally to the locked position shown in FIG. 18A. This also causes the sliding plate 870 to move laterally within the recess 880 on the bottom of the mounting plate 830, which caused the insert 850 to move, and therefore the x-ray device 100 to be forced against the upper section 815 of the cradle 810 and the constraining member 860. In this locked position, the clamping device 800 secures two different parts of the x-ray device 100 independently, providing a secure connection of the x-ray device 100 to the cradle and, therefore, to the support structure. To dismount the x-ray device 100 from the support structure, this process is merely reversed.

The clamping device 801 secures the portable x-ray device 100 to the cradle 810 in two locations: first, just below the hinge 165 using the constraining member 860; and second, by way of the registration insert 850 in the opening 175. These locations are on opposing portions of the second part 160 of the x-ray device 100, providing a robust clamp on the x-ray device 100 when the attachment device 865 pulls the x-ray device 100 into the locked position.

The clamping device 801 also provides significant tolerance for using sterile bags with the portable x-ray device 100. As can be seen in the arrangement of levers, connectors, and sliding components that form clamping device 801 as they move to the various positions depicted in FIGS. 18A-C, there is tolerance within the mechanism to allow for the thicknesses of many layers of plastic sterile bags to accumulate around the x-ray device 100, and the components of the cradle 810. This tolerance can be seen in the transition of the clamping device 801 as the components move from the locations shown in FIG. 18B to those shown in FIG. 18A where connecting member 855 (for example) moves only slightly from FIG. 18B to FIG. 18A as the attachment device 865 is locked into place. This ensures that many thicknesses of sterile bag material (a single layer being on the order of about 5 mils thick) can be placed (for example) over and around the x-ray device 100 and separately over and around the insert 850 without causing any difficulty in moving the attachment device 865 into the locked position. The layers of sterile bag material that are placed between the x-ray device 100 and the insert 850 will alter the relative position of the insert 850, the x-ray device 100, and the total lateral distance that the x-ray device 100 must be moved by the insert 850 to ensure the x-ray device 100 is properly constrained by constraining member 860. Therefore, the ability to tolerate these variations should be accounted for in the configuration of the portable x-ray device and clamping device 801. In some configurations, this tolerance can be about 5 mils, about 10 mils, about 15 mils, about 20 mils, or more even up to perhaps about 40 mils, about 45 mils, or even about 50 mils, all depending on the number of folds in the sterile bag material, and the care that is given in how it is arranged on the x-ray device and separately on the cradle. In other embodiments, this tolerance can be any range, sub-range, combination, or sub-combination of these amounts.

Another advantage of the clamping device 801 over the clamps 940 is the robustness of the clamping mechanism 801 against wear and deterioration during use. For example, one method to operate and secure the clamps 940 is to use a ratchet mechanism which has the advantage that it is easy to understand and operate, and can be easily closed by the user. During operation, however, this type of mechanism showed wear characteristics that can be unacceptable. In order to secure the x-ray device 100 on the cradle without any appreciable looseness or play in the mounting while accommodating the variations caused by a sterile bag, the ratchet mechanism needs to have small steps between each stop or position in the ratchet mechanism so that the clamps 940 can be secured on the x-ray device 100 tightly despite the variability in the conditions and quantity of draping material. But there is a trade-off between the durability of the mechanism and the ratchet step size. As the ratchet step size is reduced in order to securely clamp the x-ray device, the teeth on the gears and other components in the ratchet mechanism become smaller and more subject to wear and degradation. While a ratchet mechanism was shown to be a viable way to secure the clamps 940, it was felt that the clamping device 801 would be a better over-all solution.

The clamping device 801 can also be modified to include any of the features described in relation to any other embodiments described herein. For example, in some modifications, the surfaces can be configured so they have some significant area so that there is no feature (including features such as handles, clamping levers, and similar devices) capable of, or likely to, puncture the sterile bag if the bag is stretched across the physical feature. So the features can be designed or angled to lie close to the adjacent surface in order to avoid any features that poke out from the over-all device at large angles of about 60 degrees, about 70 degrees, about 80 degrees, or about 90 degrees. The features should also have a rounded end with a radius of at least about 2 mm, about 3 mm, about 4 mm, or even about 5 mm in order to avoid punctures of the sterile bag polymer sheet. Additionally, the features can be designed to ensure that a thin plastic sheet or membrane from a sterile bag cannot be caught, torn, stretched, or punctured by the operation of the clamping device 801.

A helpful feature found in both clamping device 801 and clamping device 940, along with cradle configuration 800 and 910, is that they do not add significant thickness to the combination of the X-ray device 100 and the respective cradle. Overall, the thickness of the combination, when measured from the top of the detector plate 140 to the bottom of the respective cradle is increased by approximately the thickness of the metal (or other material) from which that cradle is constructed. This thickness must be sufficient to provide the necessary strength for that cradle, but still be thin so that the X-ray device 100 plus the respective cradle can be easily slid under the patient or the portion of the patient's body that needs to be imaged without requiring or causing much displacement of the patient's body or body part. The thickness of the cradle material that meets both requirements can be on the order of about $\frac{1}{8}^{th}$ of an inch, or about 0.125 inches (3.175 mm). If the material were sufficiently low in density to avoid adding too much weight, a maximum thickness of perhaps about $\frac{1}{4}^{th}$ inch or about 0.25 inches (6.35 mm) can be used. Generally, the desired thickness would be a thin as possible in order to reduce both the weight of the cradle as well as the over-all thickness, so a minimum practical thickness could approach about $\frac{1}{16}^{th}$ of an inch (0.0625 inches or 1.59 mm) for the base of the cradle.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A clamping device for a portable X-ray device, comprising:
 a cradle configured to support a portion of a C-arm of a portable x-ray device;
 a mounting plate configured to support a bottom portion of the portable x-ray device;
 a registration insert configured to mate with an opening in the bottom portion of the portable x-ray device, the registration insert also configured to move laterally along the mounting plate; and
 an attachment device configured to move the registration insert to attach the portable x-ray device to the cradle.

2. The device of claim 1, wherein the cradle is configured to be connected to an external support structure for the portable x-ray device.

3. The device of claim 1, wherein the portable x-ray device is capable of being removed from or attached to the clamping device using a single hand.

4. The device of claim 1, wherein the mounting plate constrains a bottom of the portable x-ray device when it abuts the cradle.

5. The device of claim 1, further comprising sidewalls located on the sides of the mounting plate, the sidewalls configured to support a portion of the sides of the bottom portion of the portable x-ray device.

6. The device of claim 5, wherein the sidewalls extend along the length of the mounting plates and are connected to an upper section of the cradle containing the restraint.

7. The device of claim 1, wherein the attachment device further comprises a handle that can be accessed or operated through an opening in the cradle and through an opening in the x-ray device.

8. The device of claim 7, wherein the handle is configured to be moved by an operator to lock or unlock the portable x-ray device to the cradle.

9. The device of claim 1, wherein the thickness of the cradle is less than about 0.125 inches.

10. An x-ray system, comprising:
 a portable X-ray device having a C-arm and a bottom portion;
 a support structure for the portable X-ray device;
 a clamping device comprising:
  a cradle connected to the support structure and configured to support a portion of a C-arm of a portable x-ray device;
  a mounting plate configured to support a bottom portion of the portable x-ray device;
  a registration insert configured to mate with an opening in the bottom portion of the portable x-ray device, the registration insert also configured to move laterally along the mounting plate; and
  an attachment device configured to move the registration insert to attach the portable x-ray device to the cradle.

11. The system of claim 10, wherein the supporting structure comprising an extension arm configured to be connected to the cradle.

12. The system of claim 10, wherein the portable x-ray device is capable of being removed from or attached to the clamping device using a single hand.

13. The system of claim 10, wherein the mounting plate constrains a bottom of the portable x-ray device when it abuts the cradle.

14. The system of claim 10, further comprising sidewalls located on the sides of the mounting plate, the sidewalls configured to support a portion of the sides of the bottom portion of the portable x-ray device.

15. The system of claim 14, wherein the sidewalls extend along the length of the mounting plates and are connected to an upper section of the cradle containing the restraint.

16. The system of claim 10, wherein the attachment device further comprises a handle that can be accessed or operated through an opening in the cradle and through an opening in the x-ray device.

17. The system of claim 10, wherein the handle is configured to be moved by an operator to lock or unlock the portable x-ray device to the cradle.

18. The system of claim 10, wherein the thickness of the cradle is less than about 0.125 inches.

19. A method of imaging, comprising:
attaching a portable x-ray device having a C-arm and a bottom to a supporting structure with a single hand using a clamping device comprising:
a cradle configured to support a portion of a C-arm of a portable x-ray device;
a mounting plate configured to support a bottom portion of the portable x-ray device;
a registration insert configured to mate with an opening in the bottom portion of the portable x-ray device, the registration insert also configured to move laterally along the mounting plate; and
an attachment device configured to move the registration insert to attach the portable x-ray device to the cradle;
locking the portable x-ray device onto the cradle by pulling a handle of the attachment device and moving the registration insert relative to the mounting plate; and
imaging an object using the portable x-ray device.

20. The method of claim 19, wherein the handle can be accessed or operated through an opening in the cradle and through an opening in the portable x-ray device.

* * * * *